(12) United States Patent
Steffan et al.

(10) Patent No.: US 7,169,591 B1
(45) Date of Patent: Jan. 30, 2007

(54) PREPARATION OF ENANTIO-SPECIFIC EPOXIDES

(75) Inventors: Robert J. Steffan, Wrightstown, PA (US); Kevin R. McClay, Hightstown, NJ (US)

(73) Assignee: Shaw Environmental & Infrastructure, Inc., Lawrenceville, NJ (US)

( * ) Notice: Subject to any disclaimer, the term of this patent is extended or adjusted under 35 U.S.C. 154(b) by 0 days.

(21) Appl. No.: 10/088,991

(22) PCT Filed: May 26, 2000

(86) PCT No.: PCT/US00/14637

§ 371 (c)(1),
(2), (4) Date: Sep. 16, 2002

(87) PCT Pub. No.: WO00/73425

PCT Pub. Date: Dec. 7, 2000

Related U.S. Application Data

(60) Provisional application No. 60/136,602, filed on May 28, 1999.

(51) Int. Cl.
*C12P 17/00* (2006.01)
(52) U.S. Cl. ............ 435/189; 435/117; 435/123; 435/280; 435/41; 435/132
(58) Field of Classification Search .......... 435/189, 435/117, 123, 280, 41, 132
See application file for complete search history.

(56) References Cited

U.S. PATENT DOCUMENTS

| | | | |
|---|---|---|---|
| 4,269,940 A | 5/1981 | Patel et al. | |
| 4,347,319 A | 8/1982 | Hou et al. | |
| 5,358,860 A | 10/1994 | Hager et al. | |

OTHER PUBLICATIONS

Archelas et al., Annu Rev Microbiol, 51:491-525 (1997).
Broun et al., Science, 282:1315-1317 (1998).
Byrne et al., Gene, 154:65-70 (1995).
Claffey et al., Tetrahedon Letters, 37:7929-7932 (1996).
Claffey et al., Tetrahedon: Asymmetry, 8:3715-3716 (1997).
de Lorenz et al., Gene, 123:17-24 (1993).
O'Connor et al.. Applied and Enviromental Microbiology, 63:4287-4291 (1997).
Eaton et al., Journal of Bacteriology, 177:6983-6988 (1995).
Ensley et al., Science, 222:167-169 (1983).
Ensley et al., Applied and Environmental Microbiology, 60:285-290 (1994).
Feig et al., Chem. Rev., 94:759-805 (1994).
Fox et al., Biochemistry, 29:6419-6427 (1990).
Habets-Crutzen et al., Enzyme Microb Technol, 7:17-21 (1985).
Habets-Crutzen et al., Appl Microbiol Biotechnol, 20:245-250 (1984).
Herrero et al., Journal of Bacteriology, 172:6557-6567 (1990).
Kok et al., Journal of Bacteriology, 179:4270-4276 (1997).
Kok et al., Journal of Bacteriology, 176:6566-6571 (1994).
Lalonde, Chemical Engineering, 9:108-112 (1997).
Lund et al, Eur J Biochem, 147:297-305 (1985).
Malakul et al., Applied and Environmental Microbiology, 64:4610-4613 (1998).
May et al., Journal of the American Chemical Society, 98:7856-7858 (1976).
McClay et al., Applied and Environmental Microbiology, 61:3479-3481 (1995).
McClay et al., The 97th General Meeting of ASM, Abstract K36, 348 (1997).
McClay et al., Applied and Environmental Microbiology, 62:2716-2722 (1996).
Murdock et al., Bio/Technology, 11:381-386 (1993).
Mermod et al., Journal of Bacteriology, 167:447-454 (1986).
Murrell, Biodegredation, 5:145-159 (1994).
Ono et al., Journal of Molecular Catalysis, 61:113-122 (1990).
Panke et al., Applied and Environmental Microbiology, 64:2032-2043 (1998).
Pikus et al., Biochemistry, 35:9106-9119 (1996).
Pikus et al., Biochemistry, 36:9283-9289 (1997).
Rosenzweig et al., Proteins, 29:141-152 (1997).
Shields et al., Applied and Environmental Microbiology, 55:1624-1629 (1989).
Stinson, CENEAR, 76:1-18 (1998).
van Hylckama Vlieg et al., Applied and Environmental Microbiology, 62:3304-3312 (1996).
Wackett et al., Applied and Environmental Microbiology, 54:1703-1708 (1988).
Wade, Organic Chemistry, 504-506 (1990).
Whited et al., Journal of Bacteriology, 173:3010-3016 (1991).
Yen et al., Journal of Bacteriology, 173:5315-5327 (1991).
Yen et al., Journal of Bacteriology, 174:7253-7261 (1992).
Zhou et al., Applied and Environmental Microbiology, 65:1589-1595 (1999).
Zhou et al., FEBS Letters, 430:181-185 (1998).

*Primary Examiner*—L Blaine Lankford
(74) *Attorney, Agent, or Firm*—Synnestvedt & Lechner LLP

(57) ABSTRACT

A method for converting alkenes into epoxides and, particularly, to convert alkenes into enantio-specific epoxides by the use of enzymes which may be in their naturally-occuring (native) form or in mutated form, such as a native or mutated non-haem diiron-containing monooxygenase, and novel compounds produced thereby.

10 Claims, 18 Drawing Sheets

FIGURE 1

```
      61
T4MO- IQREKDAGAYSVKAALERAKIYENSDPGWISTLKSHYGAIAVGEYAAVTGEGRMARFSKA
T3MO1-IQREKDAGAYSVKAALERSRMFEDADPGWLSILKAHYGAIALGEYAAMSAEAARMARFGRA
T3MO2-VQREKDSGAYSVKAALERSQIYEKADPGWKSVMKQHYGAISLAEYAAFQRLRLERCACRR
Toxy- IQREKDSGAYSIKAALERDGFVDRADPGWVSTMQLHFGAIALEEYAASTAEAARMARFAKA
PY2A- VQRDKEASVGAIREAMVRAKAYEKLDDGHKATSHLHMGTITMVEHMAVTMQSRFVRFAPS
AMO2-               GFLDGAVRTREATRIEPRFAEAMKIMVPQLTNAEYQAVAG
MMO-                TLLDGLTRLGAGNKVHPRWGETMKVISNFLEVGEYNAIAA
T2MO-               VIEAFAQNNGQLGISDARYVNALKLFIQGVTPLEYNAHRG 122
T4MO- PGNR*NMATFGMDELRHGQLQLFFPHEYCKKDRQFDWAWRAYHSNEWAAIAAKHFFDDII
T3MO1-PGMR*NMAITFGMLDENRHGQLQLYFPHDYCAKDRQFDWAHKAYHTNEWGAIAAARSTFDDLF
T3MO2-LQGCANMATMGSLDEIRHGQIQLYFPHEHVSKDRQFDWAAKAYHTNEWAAIAARHFFDDIM
Toxy- PGNR*NMATFGMDENRHGQIQLYFPYANVKRSRKWDWAHKAIHTNEWAAIAARSFFDNMM
PY2A- ARWRS*LGAFGMLDETRHTQLDLRFSHDLLNDSPSFDWSQRAFHTDEWAVLATRNLFDDIM
AMO2-          LDEVRHAQLEMTLRNYY      RGLYQHPAGLVSIGEFQHFNT
MMO-           LDEIRHTHQCAFINHYY      RTRAIGPIWKGMKREVSDGFI
T2MO-          IDELRHYQTETHAISHY      NHWFDRVWYLSVPKSFFEDAC 183
T4MO- *TGRDAISVAIMLTFSFETGFTNMQFLGLAADAAEAGDYTFANLISSIQTDESRHAQQGGP
T3MO1-*MSRSAIDIAIMLTFAFETGFTNMQFLGLAADAAEAGDFTFASLISSIQTDESRHAQIGGP
T3MO2-*MTRDAISVGIMLTFGFETGFTNMQFLGLAADAAEAGDHTFASLISSIQTDESRHAQIGGP
Toxy- *MTRDSVAVSIMLTFAFETGFTNMQFLGLAADAAEAGDHTFASLISSIQTDESRHAQQGGP
PY2A- MLNADCVEAALATSLTLEHGFTNIQFVALASDAMEAGDVNFSNLLSSIQTDEARHAQLGFP
AMO2-          IDLNIVAETAFTNILLVATPQVAVANGDNAMASVFLSIQ
MMO-           VNLQLVGDFCFTNPLIVAVTEWAIGNGDEITPTVFLSVE
T2MO-          TAVSFSFEYVLTNLLFVPFMSSGAPHNGDMSTVTFGFSAQ
```

Figure 1. Multiple sequence alignment of the hydroxylase sub-unit of T4MO from *P. mendocina* KR1, T3MO(1) of *B. pickettii*, T3MO(2) of *B. cepacia*, Toluene/o-xylene oxygenase of *P. stutzeri* OX1, Alkene monooxygenase of *Xanthobacter* PY2, AMO(2) of *R. rhodochrous* B276, MMO of *M. capsulatus* (Bath), and T2MO of *Pseudomonas* JS150. Numbering of the sequences reflects the coordinates of T4MO. Moieties that have been mutated in this study, and the analogous moieties in the other oxygenases are shown in red. The sequences were retrieved from GenBank, and manually aligned.

FIGURE 15 – AMINO ACID SEQUENCES OF TMO

FIGURE 15-A  TMO A

MAMHPRKDWYELTRATNWTPSYVTEEQLFPERMSGHMGIPLEKWESYDEPYKTS
YPEYVSIQREKDAGAYSVKAALERAKIYENSDPGWISTLKSHYGAIAVGEYAAVTG
EGRMARFSKAPGNRNMATFGMMDELRHGQLQLFFPHEYCKKDRQFDWAWRAYH
SNEWAAIAAKHFFDDIITGRDAISVAIMLTFSFETGFTNMQFLGLAADAAEAGDYTF
ANLISSIQTDESRHAQQGGPALQLLIENGKREEAQKKVDMAIWRAWRLFAVLTGPV
MDYYTPLEDRSQSFKEFMYEWIIGQFERSLIDLGLDKPWYWDLFLKDIDELHHSYH
MGVLDWRTTAWWNPAAGVTPEERDWLEEKYPGWNKRWGRCWDVITENVLNDR
MDLVSPETLPSVCNMSQIPLVGVPGDDWNIEVFSLEHNGRLYHFGSEVDRWVFQQ
DPVQYQNHMNIVDRFLAGQIQPMTLEGALKYMGFQSIEEMGKDAHDFAWADKCK
PAMKKSA

FIGURE 15-B  TMO B

MSAFPVHAAFEKDFLVQLVVVDLNDSMDQVAEKVAYHCVNRRVA

FIGURE 15-C  TMO C

MSFEKICSLDDIWVGEMETFETSDGTEVLIVNSEEHGVKAYQAMCPHQEILLSEGS
YEGGVITCRAHLWTFNDGTGHGINPDDCCLAEYPVEVKGDDIYVSTKGILPNKAHS

FIGURE 15-D  TMO D

MSTLADQALHNNNVGPIIRAGDLVEPVIETAEIDNPGKEITVEDRRAYVRIAAEGEL
ILTRKTLEEQLGRPFNMQELEINLASFAGQIQADEDQIRFYFDKTM

FIGURE 15-E  TMO E

MSFESKKPMRTWSHLAEMRKKPSEYDIVSRKLHYSTNNPDSPWELSPDSPMNLWY
KQYRNASPLKHDNWDAFTDPDQLVYRTYNLMQDGQESYVQSLFDQFNEREHDQ
MVREGWEHTMARCYSPLRYLFHCLQMSSAYVQQMAPASTISNCCILQTADSLRWL
THTAYRTHELSLTYPDAGLGEHERELWEKEPGWQGLRELMEKQLTAFDWGEAFV
SLNLVVKPMIVESIFKPLQQQAWENNDTLLPLLIDSQLKDAERHSRWSKALVKHAL
ENPDNHAVIEGWIEKWRPLADRAAEAYLSMLSSDILHAQYLERSTSLRASILTV

FIGURE 15-F  TMO F

MFNIQSDDLLHHFEADSNDTLLSAALRAELVFPYECNSGGCGACKIELLEGEVSNL
WPDAPGLAARELRKNRFLACQCKPLSDLKIKVINRAEGRASHPPKRFSTRVVSKRFL
SDEMFELRLEAEQKVVFSPGQYFMVDVPELGTRAYSAANPVDGNTLTLIVKAVPN
GKVSCALANETIETLQLDGPYGLSVLKTADETQSVFIAGGSGIAPMVSMVNTLIAQ
GYEKPITVFYGSRLEAELEAAETLFGWKENLKLINVSSSVVGNSEKKYPTGYVHEII
PEYMEGLLGAEFYLCGPPQMINSVQKLLMIENKVPFEAIHFDRFF

FIGURE 16-A – DNA SEQUENCE OF TMO A THROUGH E

```
   1 aagcttttaa accccacagg cacggagaac aagaatatgg cgatgcaccc acgtaaagac
  61 tggtatgaac tgaccagggc gacaaattgg acacctagct atgttaccga agagcagctt
 121 ttcccagagc ggatgtccgg tcatatgggt atcccgctgg aaaaatggga aagctatgat
 181 gagccctata agacatccta tccggagtac gtaagtatcc aacgtgaaaa ggatgcaggt
 241 gcttattcgg tgaaggcggc acttgagcgt gcaaaaattt atgagaactc tgacccaggt
 301 tggatcagca ctttgaaatc ccattacggc gccatcgcag ttggtgaata tgcagccgta
 361 accggtgaag gtcgtatggc ccgtttttca aaagcaccgg gaaatcgcaa catggctacg
 421 ttggcatga tggatgaact gcgccatggc cagttacagc tgttttttccc gcatgaatac
 481 tgtaagaagg atcgccagtt tgattgggca tggcgggcct atcacagtaa cgaatgggca
 541 gccattgctg caaagcattt ctttgatgac atcattaccg gacgtgatgc gatcagcgtt
 601 gcgatcatgt tgacgttttc attcgaaacc ggcttcacca acatgcagtt tcttgggttg
 661 gcggcagatg ccgcagaagc aggtgactac acgtttgcaa acctgatctc cagcattcaa
 721 accgatgagt cgcgtcatgc acaacagggc ggccccgcat tacagttgct gatcgaaaac
 781 ggaaaaagag aagaagccca aagaaagtc gacatggcaa tttggcgtgc ctggcgtcta
 841 tttgcggtac taaccgggcc ggttatggat tactacacgc cgttggagga ccgcagccag
 901 tcattcaagg agtttatgta cgagtggatc atcggacagt tcgaacgctc gttgatagat
 961 ctgggcttgg acaagccctg gtactgggat ctattcctca aggatattga tgagcttcac
1021 catagttatc acatgggtgt tttggactgg cgtacaaccg cttggtggaa ccctgctgcc
1081 ggggtcactc ctgaggagcg tgactggctg gaagaaaagt atccaggatg gaataaacgt
1141 tggggtcgtt gctgggatgt gatcaccgaa aacgttctca atgaccgtat ggatcttgtc
1201 tctccagaaa ccttgcccag cgtgtgcaac atgagccaga taccgctggt aggtgttcct
1261 ggtgatgact ggaatatcga agttttcagt cttgagcaca atgggcgtct ttatcatttt
1321 ggctctgaag tggatcgctg ggtattccag caagatccgg ttcagtatca aaatcatatg
1381 aatatcgtcg accgcttcct cgcaggtcag atacagccga tgactttgga aggtgccctc
1441 aaatatatgg gcttccaatc tattgaagag atgggcaaag acgcccacga ctttgcatgg
1501 gctgacaagt gcaagcctgc tatgaagaaa tcggcctgat aaattgagga atagaaaatg
1561 tcggcatttc cagttcacgc agcgtttgaa aaagatttct tggttcaact ggtagtggtg
1621 gatttaaatg attccatgga ccaggtagcg gagaaagttg cctaccattg tgttaatcgt
1681 cgtgttgctc ctcgtgaagg tgtcatgcgg gttcgaaagc atagatcaac tgagctattt
1741 ccacgggata tgaccatagc tgagagcggc cttaacccaa ctgaagtgat cgatgtggta
1801 ttcgaggagt agcgaaaatg agctttgaaa aaatctgttc cctcgacgat atctgggtag
1861 gcgaaatgga gactttcgag acgtccgatg gtaccgaagt cttaatcgtc aacagtgaag
1921 agcatggagt gaaggcctac caggcgatgt gcccccatca ggagattctg ttatctgaag
1981 gtagctacga aggtggagta attacatgcc gcgctcacct atggaccttc aatgacggaa
2041 cagggcatgg catcaaccca gatgactgtt gtcttgccga atatcctgta gaggtaaaag
2101 gcgatgatat ttacgtcagt acaaaaggca ttttaccgaa taaggcacac agctaaacct
2161 gcgctagttg ttaaatccca catcagcgaa gcggctggga aagaaggat aatgtgatga
2221 gcacattggc tgatcaggct ttacataaca ataacgttgg accgattatc cgtgctggtg
2281 atctcgtgga accagtgatt gaaacagctg aaatcgataa tccgggaaaa gagatcacag
2341 ttgaagatag gcgggcttat gtacgcatcg cagcagaagg cgaactgata ttgactcgaa
2401 aaaccttgga agagcagttg ggtcgcccgt tcaacatgca ggaactagaa atcaatctgg
2461 cgtcctttgc aggacagatc caagccgacg aagaccagat tcgcttctac ttttgataaaa
```

FIGURE 16-A (continued)

```
2521 ccatgtaagg agggcaccat gagctttgaa tccaagaaac cgatgcgtac atggagccac
2581 ctggccgaaa tgagaaagaa gccaagtgag tacgatattg tctcacgcaa gcttcactac
2641 agtaccaaca atcccgattc accctgggag ctgagccccg atagcccaat gaatctgtgg
2701 tacaagcagt accgtaacgc atcgccattg aaacacgata actgggatgc ttttactgat
2761 cctgaccaac ttgtataccg cacctacaac ctgatgcagg atggtcagga atcttatgtg
2821 cagagtctgt tcgatcaatt caatgagcgc gaacatgacc aaatggtgcg ggagggctgg
2881 gagcacacaa tggcccgctg ttattccccg ttgcgctatc tgttccactg cctgcagatg
2941 tcgtcggcct atgttcagca gatggcgccg gcgagcacaa tctcaaattg ctgcatcctt
3001 caaactgctg acagcctgcg atggttgacg cacaccgcct accgaacgca cgaactcagt
3061 cttacttatc cggatgctgg tttaggtgag cacgagcgag aactgtggga gaaagagccg
3121 ggttggcagg ggctgcgtga attgatggag aagcaactaa ctgcttttga ttggggagag
3181 gcttttgtca gtctaaattt ggtggtcaag ccaatgattg tcgagagtat tttcaaacca
3241 ctgcagcagc aagcatggga aaataacgat accttgcttc ctctgttgat tgacagtcag
3301 ctgaaagatg ccgagcgtca tagtcgttgg tcgaaagcac ttgtaaaaca tgcgctggaa
3361 aaccccgata atcacgctgt aattgaaggt tggattgaaa agtggcgccc cttggctgac
3421 agggcagctg aagcttacct gagtatgcta tctagcgaca ttttgcacgc tcaatatctt
3481 gagcgtagta cctcattgag ggcatccata cttacggtct gattacgcgc cgtttgggtc
3541 ctattggtgg gtcttcccct tcggcattgc tgaaggggct ttttagagac gttatctatg
3601 ttcaatatt
```

FIGURE 16-B - DNA SEQUENCE OF TMO F 1 ggtcttcccc ttcggcattg ctgaaggggc tttttagaga cgttatctat gttcaatatt
   61 caatcggatg atctcctgca ccattttgag gcggatagta atgacactct acttagtgct
  121 gctctacgtg ctgaattggt atttccatat gagtgtaact caggagggtg cggcgcatgt
  181 aagatcgagc tgcttgaggg agaggtctct aacctatggc ctgatgcacc aggattagcc
  241 gcccgtgaac tccgtaagaa tcgttttttg gcgtgccagt gcaaaccatt atccgacctc
  301 aaaattaagg tcattaaccg tgcggaggga cgtgcttcac atcccccaa acgtttctcg
  361 actcgagtag ttagtaagcg cttcctctct gacgagatgt ttgagctgcg acttgaagcg
  421 gaacagaaag tggtgttttc accagggcaa tattttatgg ttgacgtgcc tgaactcggc
  481 accagagcat actccgcggc aaaccctgtt gatggaaaca cactaacgct gatcgtaaaa
  541 gcagtgccga atgggaaggt atcctgcgca ctcgcaaatg aaactattga aacacttcag
  601 ttggatggtc cttacgggct gtcagtatta aaaactgcgg atgaaactca atccgtcttt
  661 atcgctgggg ggtcaggtat cgcgccgatg gtgtcgatgg tgaatacgct gattgcccaa
  721 gggtatgaaa aaccgattac ggtgtttttac ggttcacggc tagaagctga actggaagcg
  781 gccgaaaccc tgtttgggtg gaaagaaaat ttaaaactga ttaatgtgtc gtcgagcgtg
  841 gtgggtaact cggagaaaaa gtatccgacc ggttatgtcc atgagataat tcctgaatac
  901 atggaggggc tgctaggtgc cgagttctat ctgtgcggcc cgccgcagat gattaactcc
  961 gtccagaagt tgcttatgat tgaaaataaa gtaccgttcg aagcgattca ttttgatagg
 1021 ttcttttaaa attaataagc aatagttggt tttagtagaa ttttcagtgg cgtaatgtcg
 1081 gcgctaagga actccgaata agcctgcacc aatacggcag tagcctgttc aatgtgttct
 1141 cagcgcagcc gcagccagct gattcgtcca gtagcccggg

PREPARATION OF ENANTIO-SPECIFIC EPOXIDES

CROSS-REFERENCE TO RELATED APPLICATIONS

This application is a U.S. national stage application based on International Application No. PCT/US00/14637, filed May 26, 2000, which claims priority to U.S. Provisional Application No. 60/136,602, filed May 28, 1999.

FIELD OF THE INVENTION

This invention relates to methods for converting alkenes into epoxides. More particularly, the present invention relates to converting alkenes into enantio-specific epoxides by the use of enzymes which may be in their naturally-occurring (native) form or in mutated form. The present invention is additionally directed to novel compounds produced by such enzymes.

Epoxides

The reactivity of epoxides makes them useful and important intermediates for a number of industrial chemical syntheses, including the production of pharmaceuticals, agrochemicals, and polymers. A classic method for synthesizing racemic epoxides is to expose alkenes to peroxyacids, such as peroxybenzoic acid (Wade, *Organic Chemistry*, 504–506, Prentice-Hall, Inc. (1990)). In a single step, the compounds react, yielding epoxides and benzoic acid. Alternately, epoxides can be formed starting with chloro-alcohols that have their halogen and hydroxyl groups located on adjoining carbons (Wade, supra). The addition of sodium hydroxide initiates an $SN_2$ attack, which displaces the halogen, resulting in epoxide formation. The epoxides formed by this reaction have the same atoms and covalent bonds, but differ in their three-dimensional structure and are referred to as "stereoisomers." If one stereoisomer is a non-superimposable mirror image of another stereoisomer, the stereoisomers are said to be "enantiomers" of each other. Each enantiomer rotates a plane of polarized light with an orientation that is opposite that of the other enantiomer. This optical activity is designated (R) or (S) under the Cahn-Ingold-Prelog Convention. The reaction methods described above result in the formation of racemic epoxides, that is, a mixture of approximately equal proportions of (R) and (S) enantiomers.

Enantio-Specific Epoxides

Although there are many applications for the use of racemic epoxides, the demand for the production of enantiomerically pure feedstocks of epoxides has increased in recent years. Between 1996 and 1997, the sale of enantio-pure pharmaceuticals increased 21%. Similar increases are expected in the agrochemical and polymer markets (Stinson, S. C., "Counting on chiral drugs,", *CENEAR*, 76:1–36 (1998)). This increased interest in enantiomeric purity arises from the observation that enantiomerically pure compounds often have appreciably different biological and physical properties. For example, the (S) enantiomer of carvone gives caraway seeds their distinctive odor, whereas the (R) enantiomer is perceived as spearmint (Lalonde, J., "Enzyme catalysis: cleaner safer energy efficient," *Chem. Engineer.*, 9:108–112 (1997)). Similarly, (S)-Thalidomide can cause severe birth defects, while (R)-Thalidomide is a safe and effective sedative (Lalonde, supra). These dramatic differences have led the Food and Drug Administration to require each enantiomer of a racemic drug to be tested individually prior to receiving approval (Lalonde, supra). This greatly increases the cost of bringing a new drug to market. By producing enantiomerically pure intermediates for drug synthesis, the number of isomers of a new drug that require testing prior to approval can be reduced.

REPORTED DEVELOPMENTS

The synthesis of epoxides can be chemical or enzymatic in nature. Synthesis of enantiomerically pure epoxides is more complicated than the synthesis of racemic mixtures.

Chemical Synthesis of Epoxides

A recent strategy for the chemical synthesis of R- and S-butadiene monoepoxide (BME) has been developed using D- and L-mannitol as building blocks (Claffey et al., *Tetrahedron Letters*, 37:7929–7932 (1996)). In a multi-step reaction, the mannitol is sequentially treated with tosyl chloride, sodium hydroxide, sodium periodate, and methylenetriphenylphospho-niumylide. Although an 81% yield of the desired product is produced by this process, appreciable amounts of by-product volatiles such as benzene and dimethylsulfoxide are produced also. Isolating and purifying the BME from these by-products increase the costs of producing the BME. The process is capable of being modified in a manner such that the reactants in the final stages can be immobilized on a solid support. This simplifies the isolation of BME (Claffey et al., *Tetrahedron: Asymmetry*, 8:3715–3716 (1997)). The need for corrosive and toxic materials as consumable reactants and catalysts, however, ultimately results in the generation of undesirable waste products, the disposal of which increases both the cost and the potential for environmental damage inherent to the current processes for synthesizing enantio-pure epoxides.

Enzymatic Formation of Enantio-Specific Epoxides

The use of enzymes which can insert oxygen across C═C bonds with a high degree of enantio-selectivity as catalysts for epoxide synthesis has been explored with varying degrees of success. The styrene monooxygenase of *Pseudomonas* sp. strain VLB120 converts styrene to (S)-styrene oxide with an enantiomer excess of >99% (Panke et al., *Appl. Envir. Microbiol.*, 64:2032–2043 (1998)). Another enzyme, the alkane hydroxylase of *Pseudomonas oleovorans*, converts 1,7-octadiene to optically active (R) 7,8-epoxy-1-octene with an enantiomeric purity of 98% (May et al., *J. Am. Chem. Soc.*, 98:7856–7858 (1976)). The 7,8-epoxy-1-octene then undergoes a second oxidation catalyzed by alkane hydroxylase to form (R)-1,2:7,8-diepoxyoctane with an enantiomeric purity of 83%. These observations led to industrial applications for the synthesis of the drugs Metoprolol and Atenolol (Archelas et al., *Annual Review of Microbiology*, Annual Review Inc., Palo Alto, Calif., 167–186 (1997)).

Several closely related non-haem diiron monooxygenase enzymes have been identified and shown to oxidize a wide range of hydrocarbons. Although the amino acid sequences and apparent physical structures of these enzymes are very similar (Zhou et al., *FEBS Letters*, 430:181–185 (1998)), their substrate ranges vary considerably.

The recent interest in synthesizing enantiomerically-pure pharmaceuticals and agricultural chemicals (Stinson, *Chemical and Engineering News*, 76:1–136 (1998)) have led researchers to begin evaluating a variety of enzymatic reactions to evaluate their enantio-selectivity. The diiron monooxygenase enzymes have been tested for their ability to produce enantio-pure epoxides including butene epoxide (Habets-Crutzen et al., *Appl. Microbiol. Biotechnol.*, 20:245–250 (1984)). The soluble methane monooxygenase (MMO) of *Methylosinus trichosporium* OB3b forms epoxides as a result of the initial oxidation of the environmental contaminants, trichloroethylene, dichloroethylene, and vinyl chloride (Fox et al., *Biochemistry*, 29:6419–6427 (1990); van Hylckama et al., *Appl. Environ. Microbiol.*, 62:3304–3312 (1996)). MMO also mediates the epoxidation of propene, 1-butene, 2-butene, and 1,3-butadiene, but with very low enantiomeric specificity (less than 64% of a single isomer) (Ono et al., *J. Mole. Catal.*, 61:113–122 (1990)). The epoxides formed from propene, butene, and butadiene did not undergo any further oxidation under the experimental conditions described, but the epoxides of ethene and cis-DCE are substrates for MMO (van Hylckama et al., *Appl. Environ. Microbiol.*, 62:3304–3312 (1996)). MMO is unable to oxidize the larger alkenes 1-pentene, cyclohexene, and 3-methyl-butene (Ono et al., supra). In contrast, the alkene monooxygenase of *Xanthobacter* sp. strain Py2 can form epoxides from alkenes and chlorinated alkenes, but with a high degree of enantio-selectivity. For example, oxidation of 3-chloropropene yields 80% (S) 3-chloro-1,2-epoxypropene, whereas the oxidation of 1-butene yielded 94% of the R isomer (Habets-Crutzen et al., *Enzyme Microb. Technol.*, 7:17–21 (1985); Habets-Crutzen et al., *Appl. Microbiol. Biotechnol.*, 20:245–250 (1984)). The formation of other epoxides by bacteria has been reviewed in detail elsewhere (Archelas et al., supra).

The present invention is related to the epoxidation of alkenes by enzymes which are effective in producing epoxides with high levels of enantiomeric specificity.

SUMMARY OF THE INVENTION

In one aspect, this invention provides a method for preparing an epoxide comprising contacting an alkene with an enzyme comprising a native non-haem diiron-containing monooxygenase and recovering the epoxides produced. In preferred form, the monooxygenase is a toluene monooxygenase.

In another aspect, this invention provides a method for preparing an epoxide comprising contacting an alkene with an enzyme comprising a mutated non-haem diiron-containing monooxygenase and recovering the epoxides produced. In preferred form, the monooxygenase is a toluene monooxygenase.

Another aspect of this invention provides a method for preparing an epoxide comprising contacting an alkene with a non-haem diiron-containing monooxygenase mutated by the substitution of at least one amino acid residue. In preferred form, the monooxygenase is toluene monooxygenase which is mutated by the substitution of at least one amino acid residue.

Another aspect of this invention provides a mutated form of a non-haem diiron monooxygenase which is capable of producing a different ratio of the (R) and (S) enantiomers of an epoxide relative to the ratio produced by a non-mutated form of the non-haem diiron monooxygenase.

Yet another aspect of the present invention provides a process for producing a mutated non-haem diiron monooxygenase which is capable of producing a different ratio of the (R) and (S) enantiomers of an epoxide relative to the ratio produced by a non-mutated form of the non-haem diiron monooxygenase comprising performing site-directed mutagenesis of amino acid residues located in the active site of the monooxygenase.

Yet another aspect of this invention provides a process for producing a desired ratio of epoxide enantiomers comprising contacting an alkene with a mutated non-haem diiron monooxygenase.

In yet another aspect of this invention provides a process for producing a desired ratio of epoxide enantiomers comprising contacting an alkene with a native non-haem diiron monooxygenase.

Another aspect of this invention provides novel epoxides formed by mutated non-haem diiron monooxygenase.

BRIEF DESCRIPTION OF THE DRAWINGS

FIG. 1 is a multiple sequence alignment of sequence region present in a variety of different monooxygenase enzymes.

(x)—*Psuedomonas mendocina* ENVpmx1;
(closed circle)—*Pseudomonas mendocina* KR1;
(open circle)—*Pseudomonas* sp. strain ENVPC5;
(closed square)—*Burkholderia* sp. strain ENVBF1;
(open square)—*Burkholderia cepacia* G4; and
(closed triangle)—pRS202.

The data points are the result of averaging duplicate samples, with the range shown as error bars.

Figure 10:
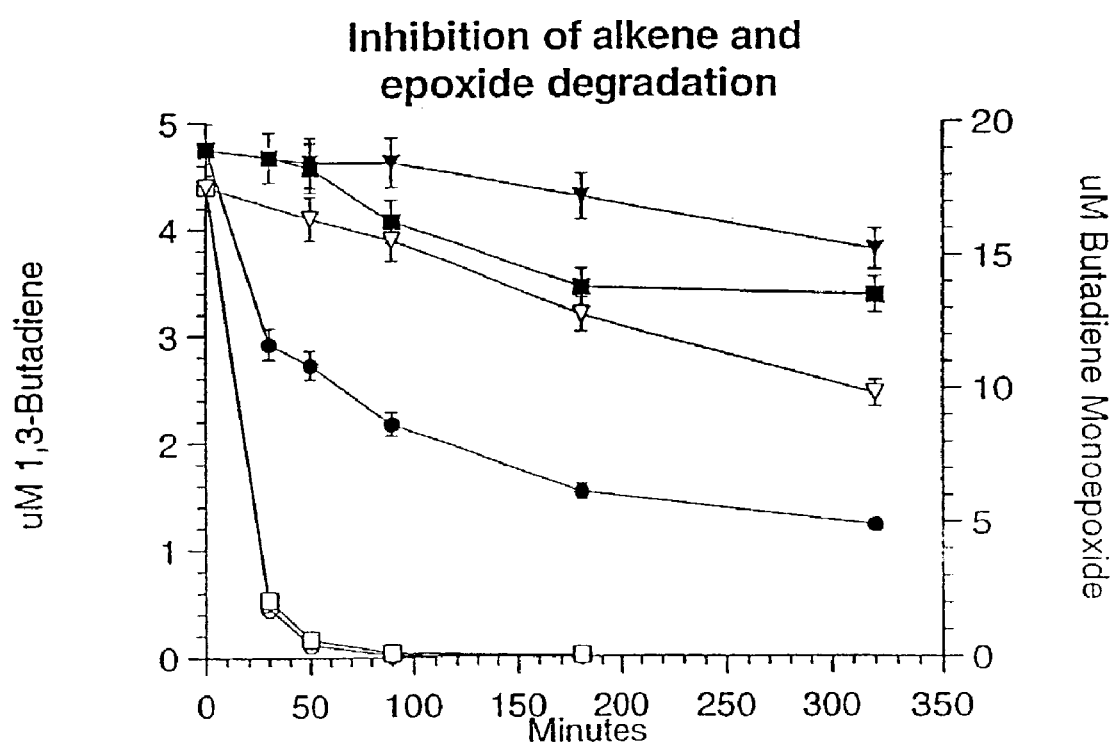

FIG. 10 shows the inhibition of the degradation of butadiene and butadiene monoepoxide (BMO) by *Burkhoderia cepacia* G4, with the following symbols representing the indicated compounds:

(open circle)—butadiene;
(open square)—butadiene in the presence of BMO;
(open triangle)—butadiene in the presence of toluene;
(closed circle)—BMO;
(closed square)—BMO in the presence of butadiene; and
(closed triangle)—BMO in the presence of toluene.

The data points are the result of averaging duplicate samples, with the range shown as error bars.

Figure 11:
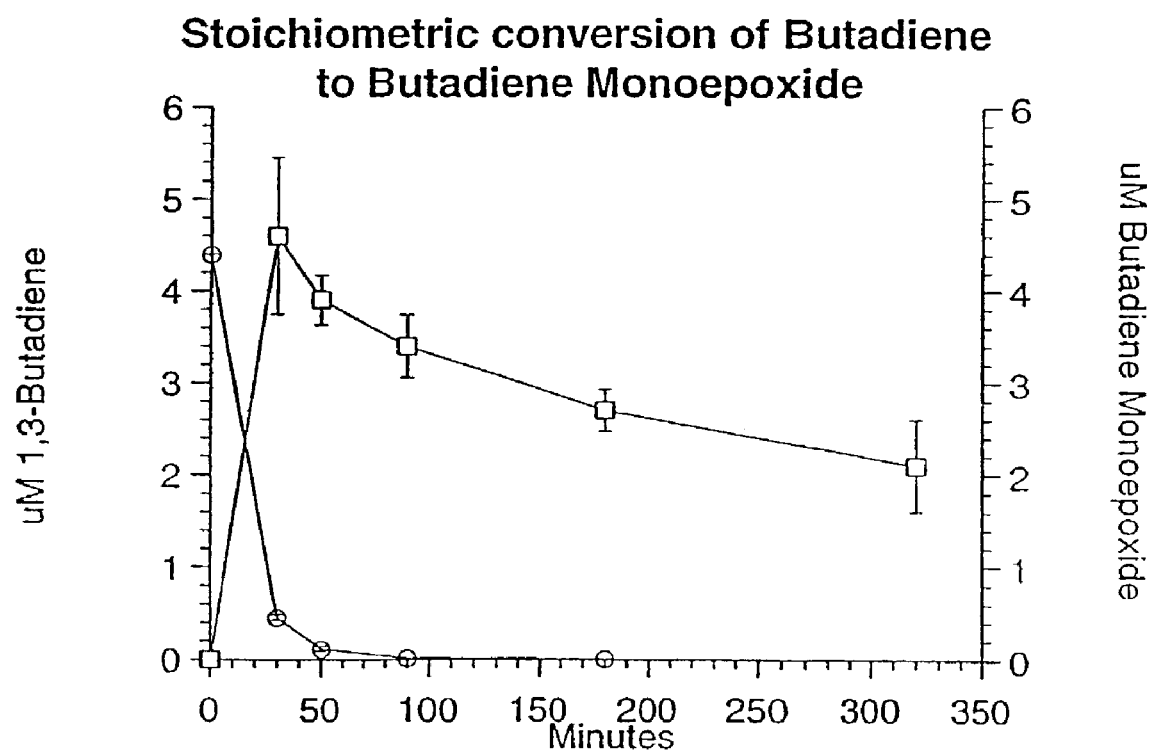

FIG. 11 shows the stoichiometric conversion of butadiene to butadiene monoepoxide by *Burkholderia cepacia* G4 in which the (open circle) represents butadiene; and the (open square) represents butadiene monoepoxide. Data points are the result of averaging duplicate samples, with the range shown as error bars.

Figure 12:
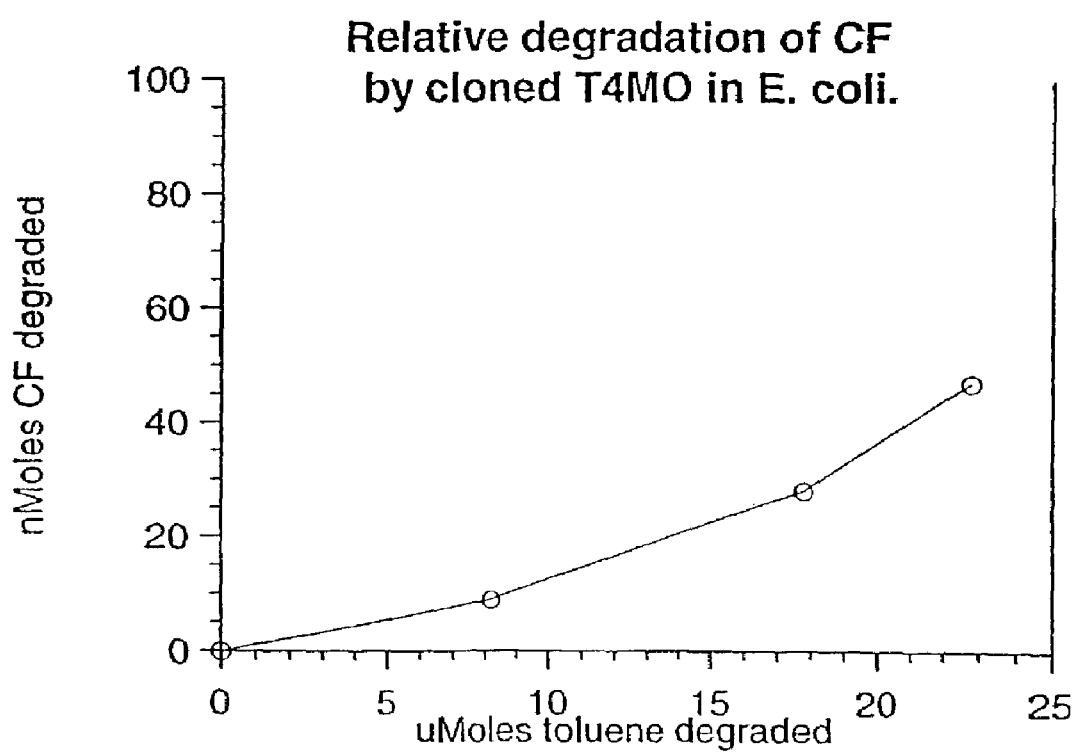
Figure 13:
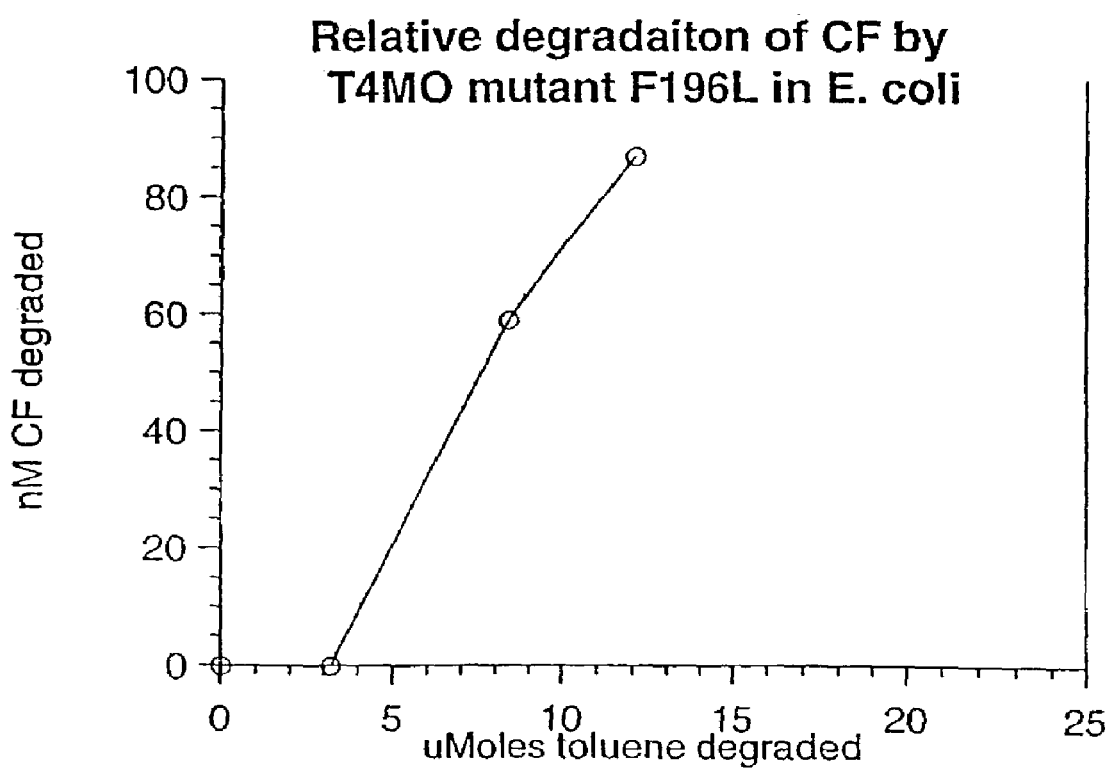

FIGS. 12 and 13 show the relative degradation of chloroform ("CF") by cloned wild type T4MO and the mutant F196L. The amount of CF and toluene present in separate samples was determined at selected time points. The data was plotted as CF degradation as a function of toluene degradation for the separate clones.

Figure 14:
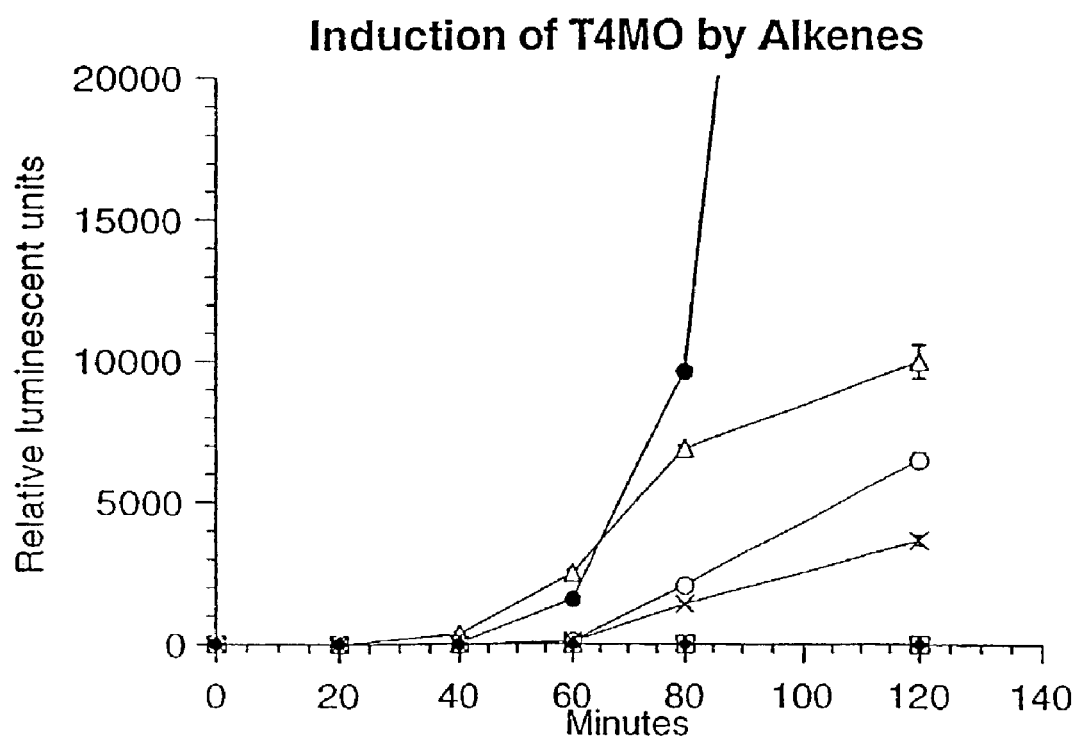

FIG. 14 shows the induction of T4MO by various alkenes and toluene with the following symbols representing the indicated alkene:

(closed circle)—2-pentene;
(open triangle)—toluene;
(open circle)—2,3-chloropropene;
(X)—butadiene diepoxide;
(closed diamond)—butadiene monoepoxide; and
(open square)—blank.

The data points are the average of duplicate samples, with the range shown as error bars. The relative light units registered by the 2-pentene sample at 120 minutes was approximately $10^5$.

FIGS. 15A to 15F show the amino acid sequence for the six gene cluster TMO A, B, C, D, E and F which encode toluene-4-monooxygenase.

FIG. 16A is the DNA sequence encoding TMO A through E of toluene-4-monooxygenase and FIG. 16B is the DNA sequence encoding TMO F of toluene-4-monooxygenase.

DETAILED DESCRIPTION OF THE INVENTION

The present invention relates to native and mutated non-haem diiron monooxygenase enzymes which convert alkenes into enantio-specific epoxides and methods for making and using these enzymes. In particular, the present invention relates to native and mutated forms of non-haem diiron monooxygenase enzymes, for example, toluene monooxygenases, which may be used to convert alkenes into enantio-specific epoxides, including the use of native enzymes in a reaction with an alkene and recovery of the products of the reaction.

The present invention is based in part on the discovery that, by changing the amino acid residues present in the active site of a non-haem diiron monooxygenase, such as toluene monooxygenase, the enantio-specificity of the epoxides produced by the oxidation of an alkene can be altered. Accordingly, the present invention provides for the preparation of mutated monooxygenase enzymes, for example, toluene monooxygenase enzymes, which produce different ratios of the enantiomeric species ((R) and (S) forms) of an epoxide relative to the ratio produced by the native enzyme. Based on the disclosure of the present invention, one of skill in the art may modify a given-non-haem diiron monooxygenase, for example, a toluene monooxygenase, in order to prepare a desired enantiomeric species of a given epoxide. The ability to prepare the desired enantiomeric species of an epoxide provides for methods of large scale production of desired epoxides which are useful in many processes, in particular, synthetic organic chemistry and pharmaceutical reactions.

Enzymes Useful in the Practice of the Invention

The enzymes used in the present invention comprise native and/or mutated non-haem diiron monooxygenases capable of oxidizing an alkene to an epoxide.

The term "oxygenase", as used herein, refers to enzymes which catalyze the incorporation of one or both atoms of a molecule of oxygen ($O_2$) into a molecule of substrate. The term "monooxygenase" refers to an enzyme which catalyzes the incorporation of one atom of oxygen into a molecule of substrate, the other oxygen being reduced to water. The term "aromatic oxygenases" refers to a preferred species of non-haem diiron monooxygenase that can oxidize a compound possessing an aromatic ring, such as, for example, toluene, benzene, and xylene or other aromatic ring-containing compounds, including compounds containing more than one aromatic ring, for example, naphthalene or anthracene.

There are a variety of methods known to those of skill in the art for determining whether an enzyme present in a microorganism can oxidize an alkene to an epoxide. These methods involve culturing a microorganism with a given alkene. Usually these methods involve introducing the grown-up microorganism into a sealed vessel, adding the alkene to the vessel followed by an incubation period. A gas or liquid sample is then taken from the vessel and analyzed using a gas or liquid chromatograph which identifies the compounds present in the sample. One can then determine whether or not an enzyme present in the microorganism has transformed the alkene into a given epoxide species and the rate of conversion of the alkene into an epoxide can be measured. A chromatograph with a chiral separation column may be used to determine the enantiomeric ratios of the epoxides present in the sample. Example 1 of the present application provides an example of such an assay which can be used to identify the ability of a given microorganism to oxidize an alkene to an epoxide and to identify the enantio-specific products produced. This same method may be used after mutagenesis to determine the change in the ratio of epoxides produced.

Although a variety of non-haem diiron monooxygenase enzymes are useful in the practice of the present invention, variants of toluene monooxygenase, are particularly preferred in the practice of the present invention. The species of toluene monooxygenase disclosed in the present application oxidize toluene at either the ortho-, meta-, and para-positions. One preferred species of toluene monooxygenase is the toluene-4-monooxygenase (T4MO) produced by *Pseudomonas mendocina* KR1. The T4MO enzyme is a multi-component enzyme comprised of six functional peptides (TmoABCDEF). The DNA sequences of tmo A-E and tmo F from *P. mendocina* KR1 have been reported previously. (Yen et al., *J. Bacteriol.*, 173:5315–5327 (1991); Yen et al., *J. Bacteriol.*, 174:7253–7261 (1992)). The holozyme functions as an electron transport chain that shuttles electrons donated from NADH to the terminal sub-unit (TmoA). TmoA is a non-haem diiron-containing hydroxylase that facilitates the regio-specific para-hydroxylation of toluene through a reactive species of oxygen. The structure of the operon encoding the enzyme system, the enzyme amino acid sequence, and the basic catalytic mechanism of the enzyme are similar to several other diiron-containing enzymes including soluble methane monooxygenase (MMO) (Murrell, *Biodegradation*, 5:145–159 (1994); Lund et al., *Eur. J. Biochem.*, 147:297–305 (1985); Zhou et al., *FEBS Letters*, 430:181–185 (1998)), alkene monooxygenases (Zhou et al., *FEBS Letters*, 430:181–185 (1998)), and toluene-2 and 3-monooxygenases (Shields et al., *Appl. Environ. Microbiol.*, 55:1624–1629 (1996); Byrne et al., *Gene*, 154:65–70 (1995)). Therefore, the elucidation of the three dimensional structure of MMO (Rosenzweig et al., *Proteins*, 29:141–152 (1997)) has provided a tool for evaluating the potential structure of the other diiron monooxygenases for which the DNA sequence is known. Knowledge of the enzyme structure provides a starting point for engineering the enzymes to alter their catalytic activity and possibly improve their enantio-selectivity.

Once an enzyme such as the toluene monooxygenases described above or an enzyme identified in the incubation assay described above has been identified, the enzyme can be either used in its native form or mutated to change the enantio-specificity of the enzyme. In particularly preferred embodiments, toluene monooxygenase is mutated to produce a modified enzyme having the desired enantio-specificity.

Inducing Mutations

As mentioned above, the present invention is based in part on the discovery that changing the amino acid residues in the active site of the non-haem diiron monooxygenase can be effective in altering the enantio-specificity of the epoxides produced by the oxidation reaction. In order to determine which amino acid residues might be involved in determining epoxide specificity, an amino acid sequence alignment of several diiron monooxygenases can be performed as illustrated in FIG. 1. The alignment in FIG. 1 was performed manually based upon an initial alignment of conserved amino acids believed to act as iron ligands (Pikus et al., *Biochemistry*, 36:9283–9289 (1997)), and previous alignments of some of the sequences performed by others (Zhou et al., *FEBS Letters*, 430:181–185 (1998); Pikus et al., *Biochemistry*, 36:9283–9289 (1997)). Based on this sequence alignment, crystallographic studies of the MMO active site (Rosenzweig et al., *Proteins*, 29:141–152 (1997)), and hypotheses of others regarding the role of some active site amino acids (see below), amino acid residues in a given non-haem diiron monooxygenase can be selected as targets for site directed mutagenesis, as disclosed in Examples 6 to 13. The effect of such mutagenesis is illustrated in Table 5 which presents the characterization of mutant T4MO isoforms discussed in the Example section showing the ability to change the enantio-specificity of the enzyme depending on the mutation in the enzyme.

A variety of known molecular biological techniques can be used to mutate the gene(s) encoding a non-haem diiron monooxygenase, such as toluene monooxygenase. General methods for the cloning, expression and mutagenesis of recombinant molecules are described in Sambrook et al. (*Molecular Cloning, A Laboratory Manual*, $2^{nd}$ edition, Cold Spring Harbor Laboratory Press, 1989) and in Ausubel et al. (eds.) (*Current Protocols in Molecular Biology*, Wiley and Sons, 1987), which are incorporated by reference. Suitable techniques include mutagenesis using a polymerase chain reaction, gapped-duplex mutagenesis, and differential hybridization of an oligonucleotide to DNA molecules differing at a single nucleotide position. For a review of suitable codon altering techniques, see Kraik, C., "Use of Oligonucleotides for site Specific Mutagenesis," *Biotechniques*, 12, Jan./Feb. 1985. Site-directed or site-specific mutagenesis procedures are disclosed in Kunkel, T. A., *Proc. Natl. Acad. Sci. USA*, 82, 488–492 (1985); Giese et al., *Science*, 236, 1315 (1987); U.S. Pat. No. 4,518,584; U.S. Pat. No. 4,959,314; Hutchinson et al., *J. Biol. Chem.*, 253: 6551 (1978); Zoller and Smith, *DNA*, 3:479–488 (1984); Oliphant et al., *Gene*, 44:177 (1986); Hutchinson et al., *Proc. Natl. Acad. Sci. USA*, 83:710 (1986). In the practice of the present invention, site-directed mutagenesis methods are preferred, especially PCR-based techniques (see Higuchi, "Using PCR to Engineer DNA," in *PCR Technology: Principles and Applications for DNA Amplification*, H. Erlich, ed., Stockton Press, Chapter 6, pp. 61–70 (1989)).

A particularly preferred method for site-directed mutagenesis utilizing PCR-based techniques is disclosed in Example 3 hereinbelow.

Alkenes

A wide variety of alkenes may be utilized for epoxidation. For example, 3, 4, 5, and 6 carbon alkenes may be oxidized to their corresponding epoxides by toluene monooxygenases. The alkenes may possess one or more double bonds, for example, dienes or trienes. Any alkene may be reacted with the native and/or mutated forms of the non-haem diiron monooxygenase and the products identified as described in Example 1. In some instances, a given alkene may be oxidized to a novel epoxide. It is also possible that the ratio of (R) to (S) enantiomer will change, in some instances, dramatically, to predominantly one or the other form of the enantiomer. Table 2 presents the specific activity of a variety of native toluene monooxygenases against alkenes and chlorinated alkenes. To determine if a given alkene can be oxidized by a given non-haem diiron monooxygenase, the procedure disclosed in Example 1 can be performed. Tables 3 and 5 present data on the ratios of epoxide enantiomers produced in this type of reaction by native (Table 3) and mutated (Table 5) forms of non-haem diiron monooxygenases. The epoxides formed in these reactions can undergo further oxidation reactions catalyzed by non-haem diiron monooxygenases or other enzymes resulting in the formation of enantio-pure diols which may be used in a variety of applications.

As examples of alkenes which can be reacted with a toluene monooxygenase, the toluene-4-monooxygenase (T4MO) of KR1, when expressed in *E. coli*, formed epoxides from 1-butene, 2-butene, 1,3-butadiene, 1-pentene, 2-pentene, and 1-hexene. The wild type organisms *R. pickettii* PKO1, *B. cepacia* G4, *P. mendocina* KR1, *Pseudomonas* sp. strain ENVBF1, and *Pseudomonas* sp. strain ENVPC5 can be used to oxidize, for example, the following non-halogenated alkenes: 1-butene, 2-butene, butadiene, 1-pentene and 2-pentene. Referring to Table 2, it is believed that the halogenated alkenes 2-chloropropene and 2,3-chloropropene are oxidized resulting in the formation of unstable epoxides. The instability of these epoxides is due to the fact that the epoxides of 2-chloroproprene and 2,3-chloropropene would have a chlorine atom associated with one of the epoxide ring carbons, and such an arrangement would result in an unstable epoxide that would undergo rapid chemical hydrolysis.

Microorganisms

A variety of microorganisms possess or can be modified to contain a non-haem diiron monooxygenase enzyme. In preferred embodiments, the microorganism is a bacterial species that naturally possesses a non-haem diiron monooxygenase or which is transformed with a DNA vector encoding a non-haem diiron monooxygenase. Microorganisms which possess non-haem diiron monooxygenases can be isolated from hydrocarbon contaminated soil by enrichment culturing, using techniques commonly used by those skilled in the art and previously described in the literature. (McClay, K., et al., 1995. *Appl. Environ. Microbiol.* 61:3479–3481.) Procedures which can be used to identify and isolate other strains of microorganisms that can be used in the practice of the invention are presented in Example 1. Examples of bacterial species which contain non-haem diiron monooxygenases and which can be used in the present invention include, for example, *Pseudomonas mendocina* KR1 (ATCC 55706); *Pseudomonas* sp. Strain ENVPC5; and *Pseudomonas* sp. Strain ENVBF1 (ATCC 55819); *B. cepacia* G4 (ATCC 53617); *B. picketti* Pk01, *Pseudomonas* sp. strain JS150, *Pseudomonas stutzeri* OX1. Other related organisms can be used also. Various exemplary strains and plasmids useful in the practice of the present invention are presented in Table 1.

The present invention additionally includes within its scope the use of one or more other microorganisms in combination with one or more of the microorganisms described herein or microorganisms genetically modified to express a native or mutated toluene monooxygenase.

For some applications, it may be desirable to introduce genes encoding an non-haem diiron monooxygenase into a microorganism that is especially suited to a given environment or which has certain growth requirements. Accordingly, microorganisms which have been transformed with a plasmid or other vector containing the gene(s) for a non-haem diiron monooxygenase may be used in the practice of the present invention. A procedure for transforming bacteria with a non-haem diiron monooxygenase gene (a toluene monooxygenase) is presented hereinbelow in Example 14. This procedure may be modified as necessary to introduce any cloned non-haem diiron monooxygenase into a given bacterial species.

The non-haem diiron monooxygenase is preferably maintained within a host microorganism that is contacted with the alkene(s). However, it is also possible to isolate the enzyme from the microorganism and use the isolated and purified enzyme, if desired.

Large Scale Preparation of Epoxides

An exemplary use of the present invention is the production of epoxides in a bioreactor which includes microorganisms comprising mutated enzymes to catalyze the conversion of alkenes to enantio-pure epoxides. By controlling the quantity of the alkene(s) introduced into the bioreactor and the contact time of the enzyme-containing microorganism with the alkene, a substantial yield of optically active epoxides may be obtained. Because the alkenes and the epoxides have vastly different boiling points (e.g., −4.5° C. for BME and 65° C. for butadiene), the parent and product compounds may be separated by distillation. Thus, the present invention represents a method for using the powerful catalytic potential of the non-haem diiron monooxygenase enzymes to generate useful products.

A variety of methods for growing and maintaining microorganisms in a bioreactor are known to those of skill in the art. The procedure used can be similar to that disclosed in B. D. Ensley and P. R. Kurisko, 1994. *Appl. Environ. Microbiol.* 60:285–290.

In an exemplary approach, alkenes are oxidized by passing the alkenes through a fluid-bed reactor that has been inoculated with bacteria such as *P. mendocina* KR1, strain ENVPC5, or strain ENVBF1 or an appropriate bacterial species possessing a mutated or transformed with a mutated non-haem diiron monooxygenase. The fluid bed reactor is, for example, a stainless steel cylinder (reactor vessel) connected to an equilibration tank, a nutrient feed tank for delivery of nutrients (e.g. soluble fertilizer) and co-substrates (e.g. toluene, phenol, benzene xylene or ethylbenzene), a pH control system consisting of tanks for caustic and acid feed controlled by chemical delivery pumps, a pH controller, and a pH probe, an oxygen delivery system consisting of a bubbleless oxygen diffuser, bottled oxygen, and an oxygen meter and probe, and an effluent collection tank. The reactor vessel is filled with granular activated carbon, sand, or other material ("reactor bed") that acts as a growth support for microbial biomass.

The reactor is operated by collecting alkene-containing water in the equilibration tank, then pumping it into the bottom of the reactor vessel at a flow rate that results in the fluidization of the granular activated carbon or sand in the reactor vessel. In one example, the reactor is operated at an influent flow rate that results in a 20% increase in the reactor bed volume. As the influent stream passes from the equilibration tank to the reactor vessel, nutrients are added to create a C:N:P ratio of approximately 100:10:1 by adding soluble fertilizer (e.g. Lesco 19,19,19) to the influent stream with a chemical metering pump. The pH of the influent stream is then adjusted by adding caustic solution or acid from the base or acid feed tanks so that the final pH of the influent is between, for example, pH 6.8- and pH 7.2. If the contaminant stream does not contain a co-substrate such as toluene, benzene, ethyl benzene, xylene or phenol, the co-substrates are added from a nutrient feed tank by using a chemical metering pump. As the alkene-containing water is passed up through the fluid bed reactor, the non-haem diiron monooxygenase-producing bacteria attached to the reactor bed material, as well as non-haem diiron monooxygenase-producing bacteria suspended in the liquid, oxidize the alkene while using toluene or phenol as a co-substrate. Gasses released from the reactor are passed through a canister of granular activated carbon to trap any volatile contaminants that are not degraded in the reactor. Alkene oxidation is measured by determining its concentration in the influent and effluent streams. For example, alkene concentrations in the streams are determined by gas chromatography/mass spectroscopy.

As an example, a reactor vessel with approximate dimensions of 1 ft diameter by 14 ft. high with an empty bed volume of 66 gal., would utilize approximately 210 lbs. of granular activated carbon or sand and the reactor would be operated at an influent flow rate of up-to 10 gal/min. (gpm). A large scale distillation apparatus is then used to separate out the epoxides from the alkenes.

The following examples are given as illustrative of the present invention.

EXAMPLES

Example 1

Determination of Ability of Different Strains to Oxidize Alkenes and Generate Epoxides Chemicals The chemicals 1-butene (99%), 2-butene (99% cis/trans mixture), 1,3-butadiene 99%, 1,3-butadiene monoepoxide (98%), 1,3-butadiene diepoxide (97%), 1-pentene (99%), 2-pentene (99% cis/trans mixture), hexene (97%), octadiene (98%), 2-chloropropene (99%), 2,3-dichloropropene (98%), 1,2-butanediol (98%), toluene, (98%) triethylamine, 4-(4-nitrobenzyl)-pyridine (PNBP), and ethylene glycol were obtained from Aldrich chemicals (Milwaukee Wis.).

Growth and Preparation of Cells

*Pseudomonas mendocina* KR1 (Yen et al., *J. Bacteriol.*, 173:5315–5327 (1991)), the T4MO mutant of KR1 *Pseudomonas mendocina* ENVpmx1 (McClay et al., *The 97$^{th}$ Annual Meeting of ASM*, Abstract K36, page 348 (1997)), *Pseudomonas pickettii* PKO1 (Byrne et al., *Gene*, 154:65–70 (1995)), *Burkholderia cepacia* G4 (Shields et al., *Appl. Environ. Microbiol.*, 55:1624–1629 (1989)), *Burkholderia* sp. strain ENVBF1 (McClay et al., *Appl. Environ. Microbiol.*, 62:2716–2722 (1996)), and *Pseudomonas* sp. strain ENVPC5 (McClay et al., 1996, supra) were cultured overnight at 30° C. in shake flasks containing basal salts medium (BSM; 10) supplemented with 0.4% sodium glutamate. Toluene was included in the vapor phase when induction of the toluene oxygenases was desired. Prior to substrate degradation assays the cultures were harvested by centrifugation and resuspended in BSM to an optical density at 550 nm ($OD_{550}$) of 2, unless otherwise indicated. A standard curve of optical density vs. protein concentration for each strain was used to calculate the amount of protein per ml of the resuspended cultures.

*Escherichia coli* DH10B containing the plasmid pRS202 (Pikus et al., *Biochemistry*, 35:9106–9119 (1996); Pikus et al., *Biochemistry*, 36:9283–9289 (1997)) was prepared in a similar manner except it was grown at 37° C. in LB media, and was resuspended to an $OD_{550}$ of 4 in LB media with 0.3–1 mM IPTG to induce expression of T4MO.

Table 1 below lists strains and plasmids useful in the practice of the invention.

TABLE 1

Strains and Plasmids

| Strains & Plasmids | Relevant Phenotype | Reference |
|---|---|---|
| Pseudomonas mendocina KR1 | T4MO | Whited and Gibson, J. Bact., 173, 3010–3016 (1991) |
| Pseudomonas mendocina ENVpmx1 | T4MO operon disrupted by lux and Tet$^r$ genes | McClay and Steffan, Abstract K36, p. 348, The 97$^{th}$ Annual Meeting of ASM, 1997 |
| Pseudomonas pickettii PKO1 | T3MO | Byrne et al., Gene, 154, 65–70 (1995) |
| Burkholderia cepacia G4 | T2MO | Sheilds et al., Appl. Environ. Microbiol., 55, 1624–1629 (1989) |
| Pseudomonas putida F1 | TDO | Wackett and Gibson, Appl. Environ. Microbiol., 54, 1703–1708 (1988) |
| Acinetobacter calcoaceticus ADP1 | Naturally competent, grows on ethanol | Kok et al., J. Bact., 179, 4270–4276 (1997) |
| Pseudomonas putida PPO200 | Cloning host, grows on ethanol | Malakul et al., Appl. Environ. Microbiol., 64, 4610–4613 (1998) |
| Burkholderia sp strain ENVBF1 | T4MO | McClay et al., Appl. Environ. Microbiol., 62, 2716–2722 (1996) |
| Pseudomonas sp strain ENVPC5 | T4MO | McClay et al., Appl. Environ. Microbiol., 62, 2716–2722 (1996) |
| E. coli DH10B | Standard cloning host, auxotroph | Gibco Inc., Gaithersburg, MD |
| BL21(DE3) | Heterotrophic strain | New England Biolabs Inc., Beverly, MA |
| XL-1 Red | Error prone DNA replication | Stratagene Inc., La Jolla, CA |
| S17-λ-pir | Mobilizes plasmids with Ori T | Herrero et al., J. Bact., 172, 6557–6567 (1990) |
| pUC18Not | Amp$^r$, standard cloning vector, MCS flanked by Not I sites | Herrero et al., J. Bact., 172, 6557–6567 (1990) |
| pUC18Sfi | Same as above, except MCS is flanked by Sfi I sites | Herrero et al., J. Bact., 172, 6557–6567 (1990) |
| pLITMUS 2 | General cloning vector | New England Biolabs Inc., Beverly, MA |
| miniTn5 km2 | Transposon delivery plasmid. Kanamycin gene flanked by Sfi sites | deLorenzo et al., Gene, 123, 17–24 (1993) |
| pTZR80 | Vector for inserting single copy of a cloned gene into the chromosome of A. calcoaceticus, under control of constitutive promoter | Kok et al., J. Bact., 176, 6566–6571 (1994) |
| pNM185 | Broad host range vector. Km$^r$, expression controlled by Xyl S | Mermod et al., J. Bact., 167, 447–454 (1986) |
| pVLT31 | Same as pNM185 except Tet$^r$, and use tac promoter controlled by lac I$^q$ | deLorenzo et al., Gene, 123, 17–24 (1993) |
| pBR322 | General cloning vector, source of Tet$^r$ gene | Kok et al., J. Bact., 176, 6566–6571 (1994) |
| pRS184f series | Derivatives of pUC18Not that express T4MO and mutants | This study |
| pRS202 series | Derivatives of pVLT31 that express T4MO and mutants | This study |
| pRS202k series | Derivatives of pNM185 that express T4MO and mutants | This study |

Alkene Degradation Assays

To determine the range of alkenes that could be degraded by the toluene monooxygenase and the degradation kinetics of the toluene monooxygenases, 5-ml aliquots of the resuspended cultures were dispensed to 25-ml serum vials and crimp sealed with Teflon™ faced septa. Gaseous alkene substrates were added as pure compounds by using a gas-tight syringe, and other alkene substrates were added from stock solutions (20% in dimethylformamide). The amount of individual alkene substrates added were as follows: 1-butene, 2-butene, and 1,3-butadiene, 2.2 µM; epoxy butane, 1,3-butadiene monoxide, and epichlorohydrine, 8 µM; 1- and 2-pentene, 9 µM; hexene, 4 µM; octadiene, 4.5 µM; 2-chloropropene, 11 µM; and, 2,3-dichloropropene, 12 µM unless otherwise indicated. The serum vials were then placed horizontally on a rotary shaker operating at 100 rpm. During incubation the temperature was maintained between 20–22° C. for the Pseudomonads and at 37° C. for E. coli. The serum vials were periodically removed from the shaker and a 10–25 µl portion of the headspace gas was withdrawn through the septa and injected onto a gas chromatograph (GC) equipped with a 30 m Vocol column (Supelco Inc. Bellefonte, Pa.) maintained at 160° C., and a flame ionization detector. This allowed the monitoring of both the alkene compounds as well as the epoxide products. The same protocol was used to detect the formation of 1,2-butanediol and butadiene diepoxide, except that 1 µl of the culture media was injected onto the column rather than the headspace gas.

Table 2 presents the results of these assays indicating the specific activity of various toluene monooxygenases found in the listed microorganisms against alkenes and chlorinated alkenes.

TABLE 2

Specific Activity of Toluene Monooxygenase
Against Alkenes and Chlorinated Alkenes

| Compound Degraded[a] | Organisms Tested | | | |
|---|---|---|---|---|
| | G4 | KR1 | ENVPC5 | ENVBF1 |
| 1,3-butadiene | 0.19 | 0.07 | 0.09 | 0.13 |
| 2-butene | 0.14 | 0.26 | 0.17 | 0.12 |
| 1-pentene | 0.08 | 0.21 | 0.15 | 0.05 |
| 2-pentene | 0.16 | 0.33 | 0.18 | 0.14 |
| 2-chloropropene | nd | 0.07 | 0.18 | 0.16 |
| 2,3-chloropropene[b] | 0.23 | 0.01 | 0.12 | 0.08 |

[a]Data presented as μM substrate degraded/minute/mg protein, as measured following 30 minutes incubation.
[b]Rate determined after 60 minutes of incubation.

Verification of Epoxide Formation

The only epoxides relevant to this study that were commercially available were 1,3-butadiene mono-, and diepoxide. These were used in GC analyses to determine retention times and to quantitate the conversion of 1,3-butadiene to the corresponding epoxides. To verify that the observed peaks were epoxides, a modification of the method of van Hylckama et al. (van Hylckama et al., Appl. Environ. Microbiol., 62:3304–3312 (1996)) was used, whereby epoxides were conjugated with PNBP to form intensely colored adducts of the epoxides. Serum vials were prepared as before, except that prior to sealing the vials, Durham tubes were placed inside the vials, with the opening of the Durham tube extending out of the liquid. The substrate was then added and the vials were incubated with moderate shaking at a 45° angle to prevent the culture liquid from entering the Durham tube. The transformation of the alkenes was monitored by GC analysis. After the rate of transformation decreased significantly, or 90% of the alkene substrate was depleted from the headspace, 400 μl of 100 mM PNBP dissolved in ethylene glycol was injected through the septa into the open end of the Durham tube. The vials were then allowed to incubate for 8 hours before they were opened and the epoxide containing PNBP withdrawn. The total volume of PNBP solution was combined with an equal volume of acetone-triethylamine (50:50) and mixed rapidly. Epoxide/PNBP adducts were detected by spectra analysis (400–700 nm).

Determining Enantiomeric Ratios

To determine the ratio of R and S isomers of the epoxides formed from the oxidation of the alkenes, samples were analyzed for the presence of the epoxides and alkenes by gas chromatography as described above. When the epoxide concentration neared its maximum, or when the 80–90% of the substrate was degraded, the enantiomeric ratio of epoxides produced was determined by injecting a sample of the headspace gas onto a GC equipped with a chiral separation column (RT-BDEXSE; Restek, Inc., Bellefonte, Pa.) and a flame ionization detector. The column was maintained at 50° C.

Table 3 provides information on the enantiomeric ratio of monoepoxides produced by enzymatically mediated oxidation of terminal alkenes.

TABLE 3

Enantiomeric Ration of Monoepoxides Produced by
Enzymatically Mediated Oxidation of Terminal Alkenes.

| Bacterial | 1,3-butadiene[a] | | 1-pentene | | 1-butene | |
|---|---|---|---|---|---|---|
| Strain | R | S | R | S | R | S |
| ENVBF1 | 22 | 78 (5) | 66.3 | 33.7 | 9.8 | 90.2 (9.8) |
| G4 | 8.1 | 91.9 (1.4) | 100 | 0 | 6.5 | 93.5 (6.5) |
| PC5 | 32.7 | 67.3 | 72.5 | 27.5 | 11.3 | 88.7 |
| KR1 | 22.4 | 77.6 | 54.2 | 45.8 | 0 | 100 (0) |
| KO1 | 19.6 | 80.4 | 64.6 | 35.4 | 8.3 | 92.7 (3) |

Values that were obtained from a single analysis are presented without a standard deviation. Values that were derived from two or more analyses are shown with the range or standard deviation.
[a]Commercially available 1,3-butadiene monoepoxide was found to be 24% R and 76% S (+/−2%).

Alkene Oxidation and Identification of Oxidation Products

Figure 2:
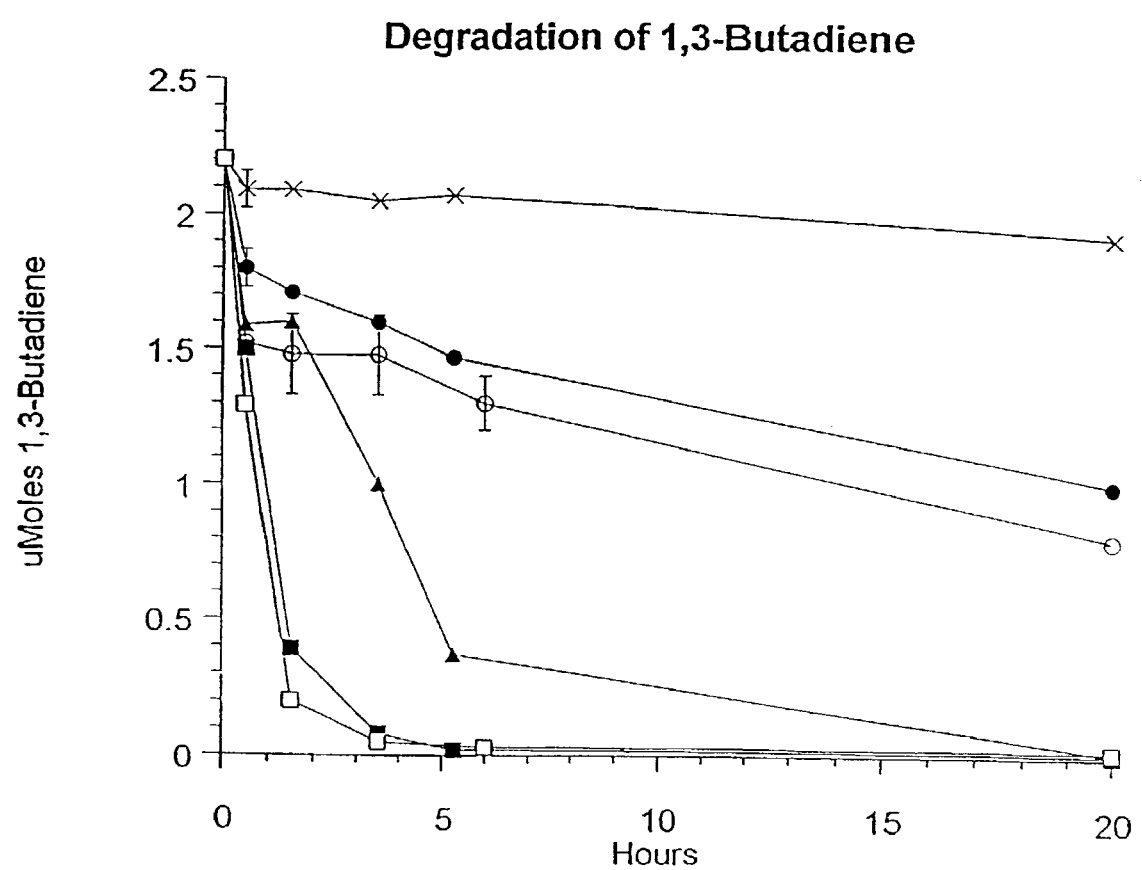
FIGS. 2 through 9 illustrate the degradation of alkenes and chlorinated alkenes by wild type organisms expressing various toluene monooxygenases and the T4MO deficient strain *Pseudomonas mendocina* ENVpmx1, with the following symbols representing the indicated organism.

Time courses for the oxidation of the alkenes examined in this study are shown in FIGS. 1–8. All of the wild type, toluene monooxygenase-producing organisms tested were able to oxidize alkenes. Greater than 95% of the added butadiene was degraded by G4 and ENVBF1 during the first five hours of incubation, whereas strains KR1 and ENVPC5 degraded only 50% of the butadiene in 20 hours (FIG. 1). Greater than 95% of the added 2-butene was degraded by all the strains tested within twenty hours, except the T4MO mutant ENVpmx1, with KR1 and ENVPC5 having faster degradation rates than G4 and ENVBF1 (FIG. 2). The levels of butadiene and 2-butene decreased by less than 10% over the course of twenty hours of incubation with the T4MO deficient strain ENVpmx1. The clone of T4MO, pRS202, degraded all of the butenes tested.

Figure 3:
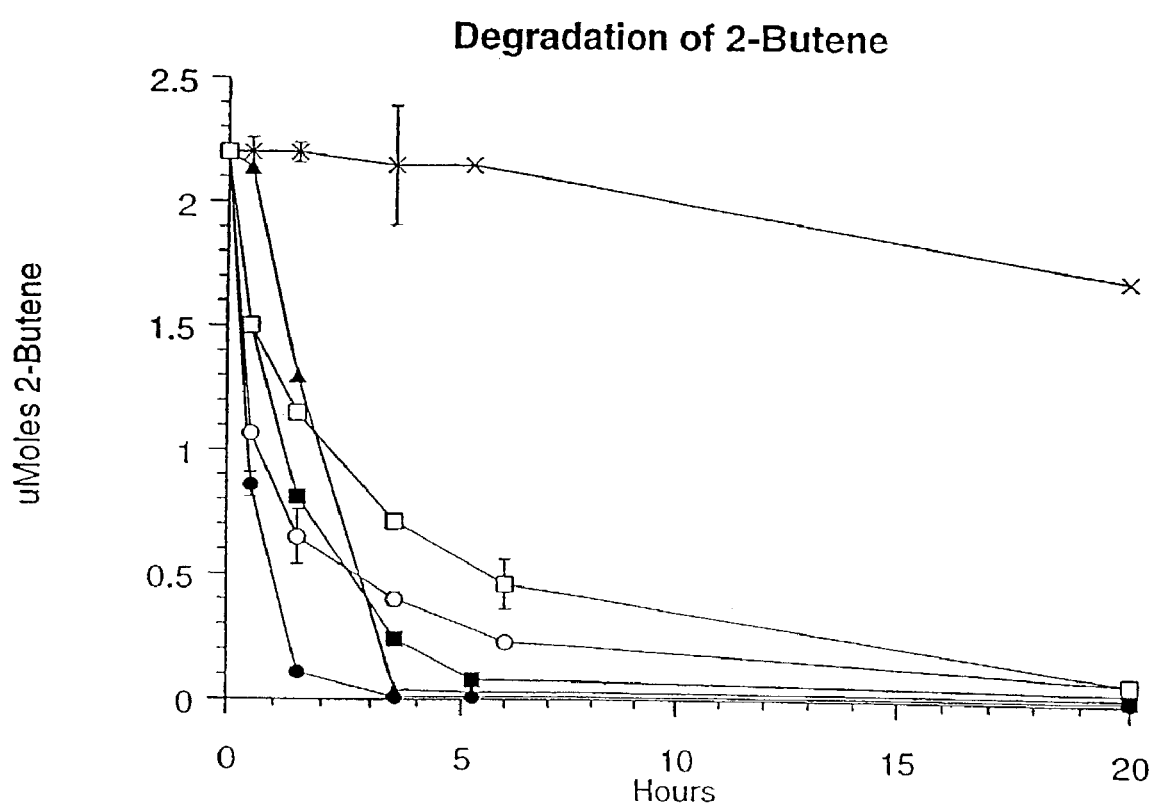
Figure 4:
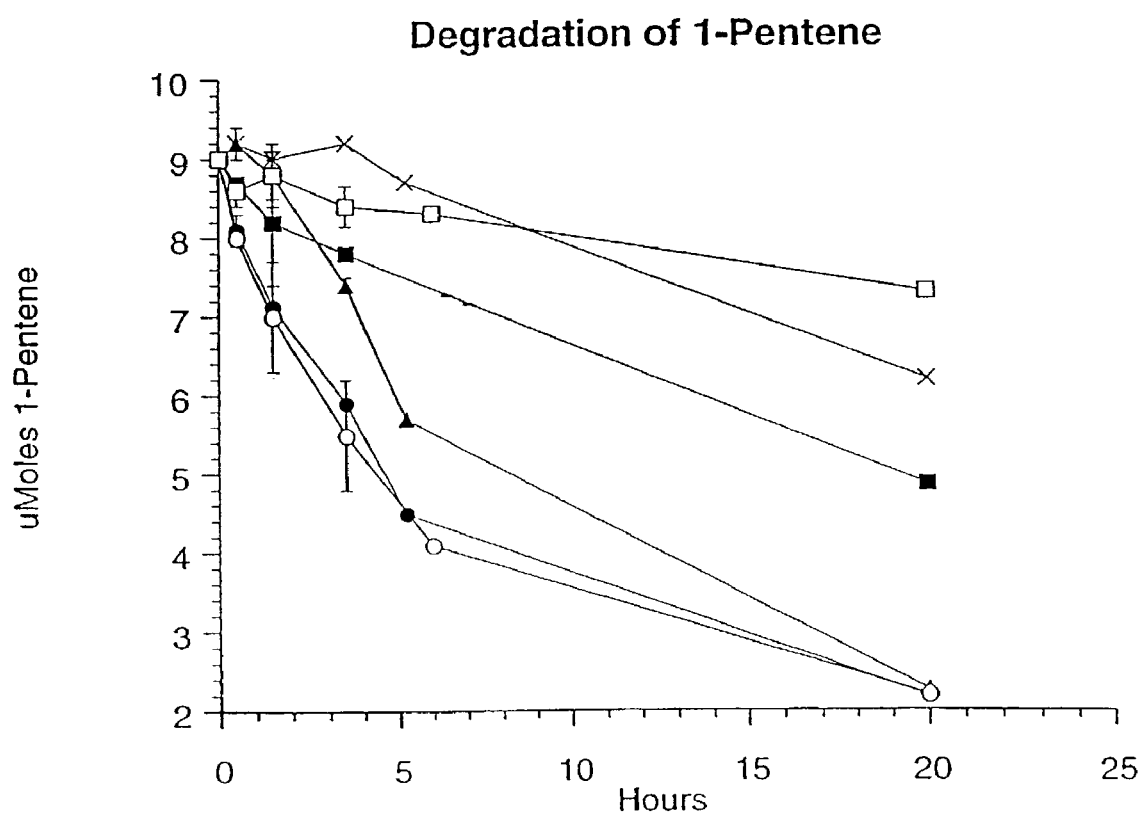

1-Pentene and 2-pentene were also efficiently degraded by all the wild type strains (FIGS. 3 and 4, respectively). The T4MO mutant ENVpmx1, following a brief lag period, degraded 2-pentene more rapidly and to a greater extent than the wild type strains (FIG. 3). ENVpmx1 also oxidized hexene and octadiene at a greater rate than the wild type strains (data not shown). E. coli (pRS202) expressing T4MO degraded 1-pentene, 2-pentene, and hexene, but did not oxidize octadiene.

Figure 5:
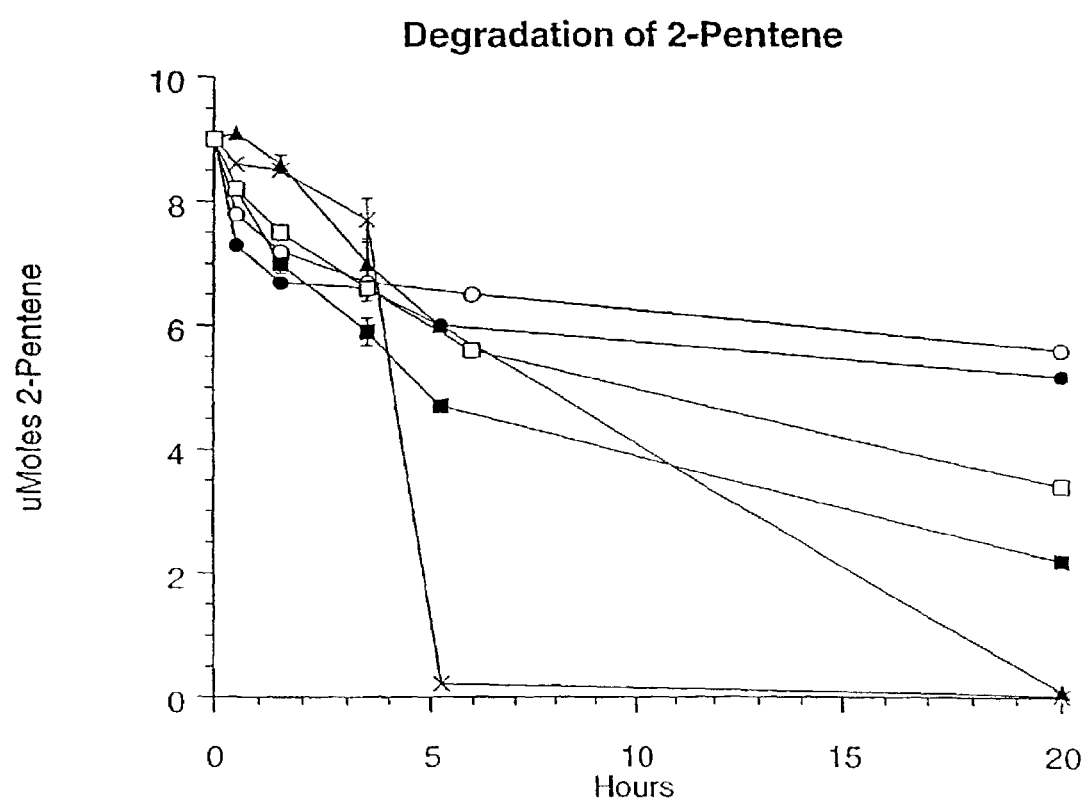

The chlorinated alkene 2-chloropropene was degraded by strains KR1, ENVPC5, and ENVBF1. Even though these organisms appear to produce the same class of toluene oxygenase (i.e., T4MO), there were differences in their ability to oxidize this compound (FIG. 5). The strains KR1 and ENVPC5 degraded 2.1 and 4 μmoles of substrate in the first 3 hours of incubation, respectively, and degraded only 0.84 and 1.0 additional μmoles, respectively, during the following 17 hours. Strain ENVBF1 degraded 2.3 μmoles of 2-chloropropene in the first 3 hours of incubation, and degraded 6.3 μmoles of substrate in the following 17 hours. It is unclear as to why ENVBF1 continued to degrade 2-chloropropene long after degradation by the other two T4MO producing organisms had ceased.

Figure 6:
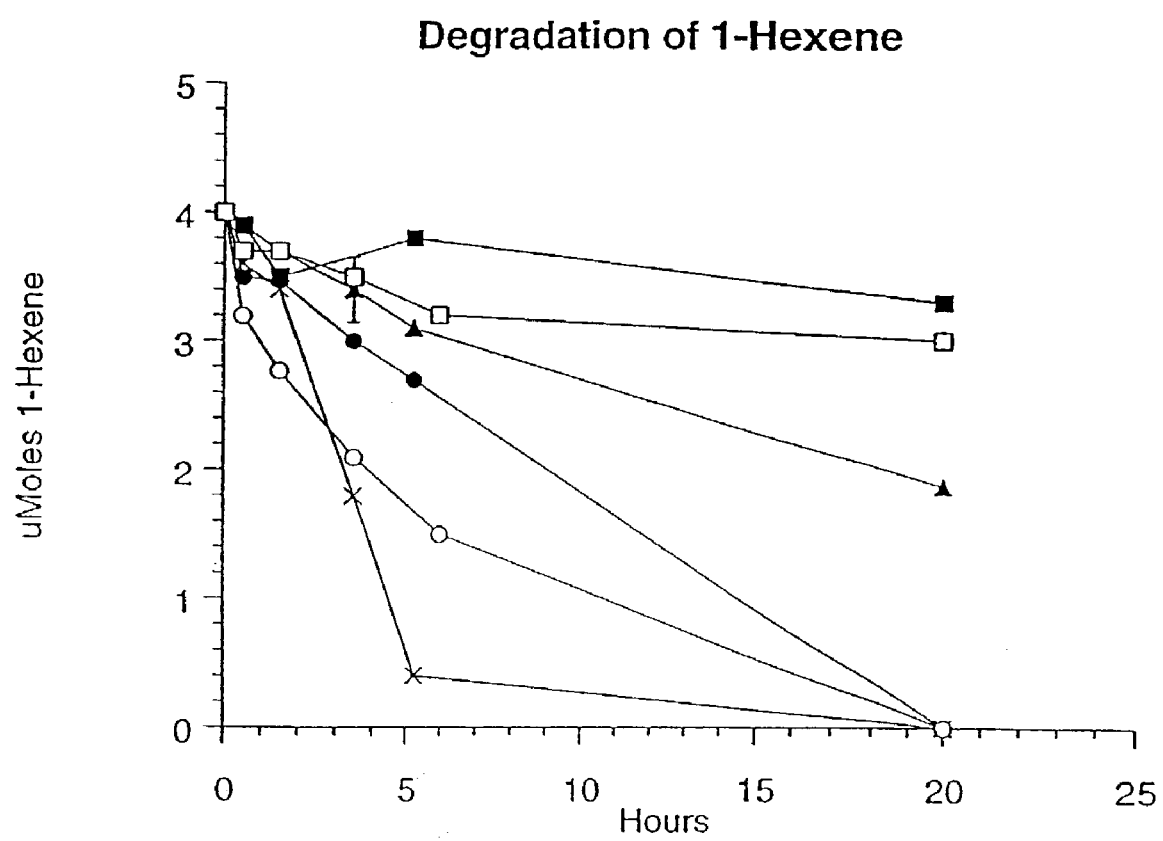

The ability of the T4MO expressing organisms to degrade alkenes was adversely affected by the presence of an additional chlorine-atom. The amount of 2,3-chloropropene oxidized by the strains KR1, ENVPC5, and ENVBF1 was 95.2%, 66.0%, and 75.6%, respectively, less than the amount of 2-chloropropene degraded by the same strains. Strain G4 was not tested on 2-chloropropene, but it was able to degrade twice as much 2,3-chlorpropene assay of the T4MO-expressing organisms (FIG. 6).

The amount of the 3 and 4 carbon alkenes oxidized by the cultures was related to the specific activity of the organisms towards the given alkene. For example, 1,3-butadiene was oxidized by G4 at an initial rate of 0.19 μM/min/mg protein (Table 2), and was oxidized to a concentration below the limits of detection within the first 6 hours of incubation (FIG. 1). KR1 had an initial oxidation rate of 0.07 μM/min/mg protein, and ultimately degraded only 1.1 μmoles (50%) of butadiene in 20 hours. With 2-butene as a substrate, KR1 had an initial oxidation rate of 0.26 μM/min/mg protein and degrading all the 2-butene in 3.5 hours. G4 oxidized 2-butene at an initial oxidation rate of only 0.14 μM/min/mg protein and required 20 hrs to degrade >95% of the added compound.

The extent of pentene and halogenated propene oxidation achieved by the individual organisms was not well correlated with the initial oxidation rate of the compound. KR1 had the greatest initial oxidation rate of 2-pentene (0.33 mM/min/mg protein) which was more than double the initial rate of 2-pentene oxidation observed in G4 and BF1 (Table 2), yet BF1 and G4 degraded more 2-pentene than KR1 during a 20 hr. incubation (FIG. 4). The high initial rate of 2-pentene oxidation by KR1 may be related to the presence of a second degradative pathway for pentene oxidation in these organisms, because the T4MO mutant of KR1, strain ENVpmx1, degraded 5 to 8 carbon alkenes efficiently. Strain ENVPC5 had higher initial oxidation rate than ENVBF1 towards 2- and 2,3-chloropropene (Table 2), but ultimately degraded less of these substrates (FIGS. 5 and 6). Unlike the case of pentene, hexene, and octadiene, there is no direct evidence to suggest that there are any additional enzymes functioning in these cells that degrade the chloropropenes. The mechanism causing the discrepancy between the specific activity and the transformation capacity is unknown.

Epoxide Formation and Degradation

GC analysis showed that during 1,3-butadiene, 2-butene, 1-pentene, and 2-pentene oxidation by the wild type organisms and *E. coli* (pRS202), a transient secondary peak was formed. A similar peak was observed during the oxidation of hexene by pRS202, but not when the wild type organisms oxidized this substrate. These secondary peaks increased in proportion to the amount of alkene oxidized, and then decreased in size following the depletion of the alkenes. The peak formed during the oxidation of butadiene co-eluted with the commercially available butadiene monoepoxide (BME). To verify that this peak and the corresponding peaks formed during the oxidation of the other alkenes were epoxides, they were conjugated with PNBP as described in the methods section. Spectral analysis showed that the PNBP conjugate of the product of butadiene oxidation had an absorbance maxima identical to the conjugate of the commercial product, and agreed closely with the data obtained for other epoxides (Fox et al., *Biochemistry*, 29:6419–6427 (1990); van Hylckama et al., supra). The conjugates of the pentenes and 2-butene had very similar absorbance spectras. From this it was concluded that the secondary peaks were authentic epoxides.

Even though the T4MO mutant ENVpmx1 efficiently oxidized pentene, hexene, and octadiene, no epoxides were detected during the oxidation of any of these compounds by this strain. Similarly, no epoxides were detected during the oxidation of hexene, octadiene, 2-chloropropene, or 2,3-chloropropene by the wild type organisms.

Figure 8:
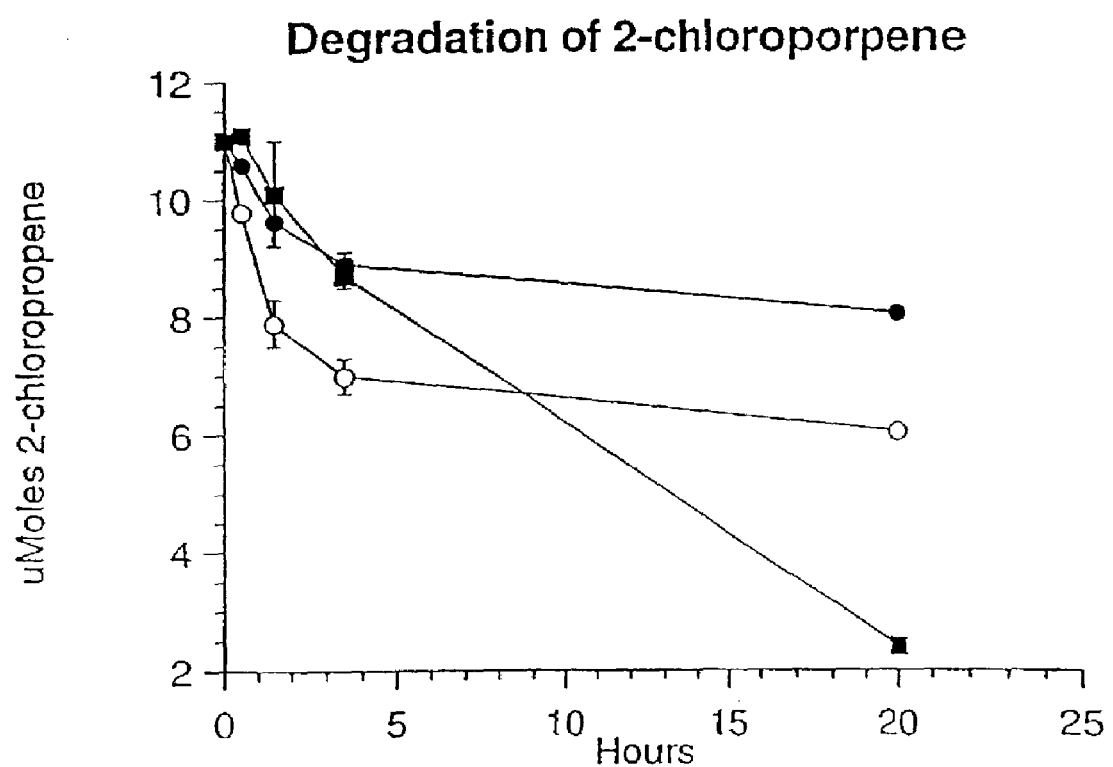
Figure 9:
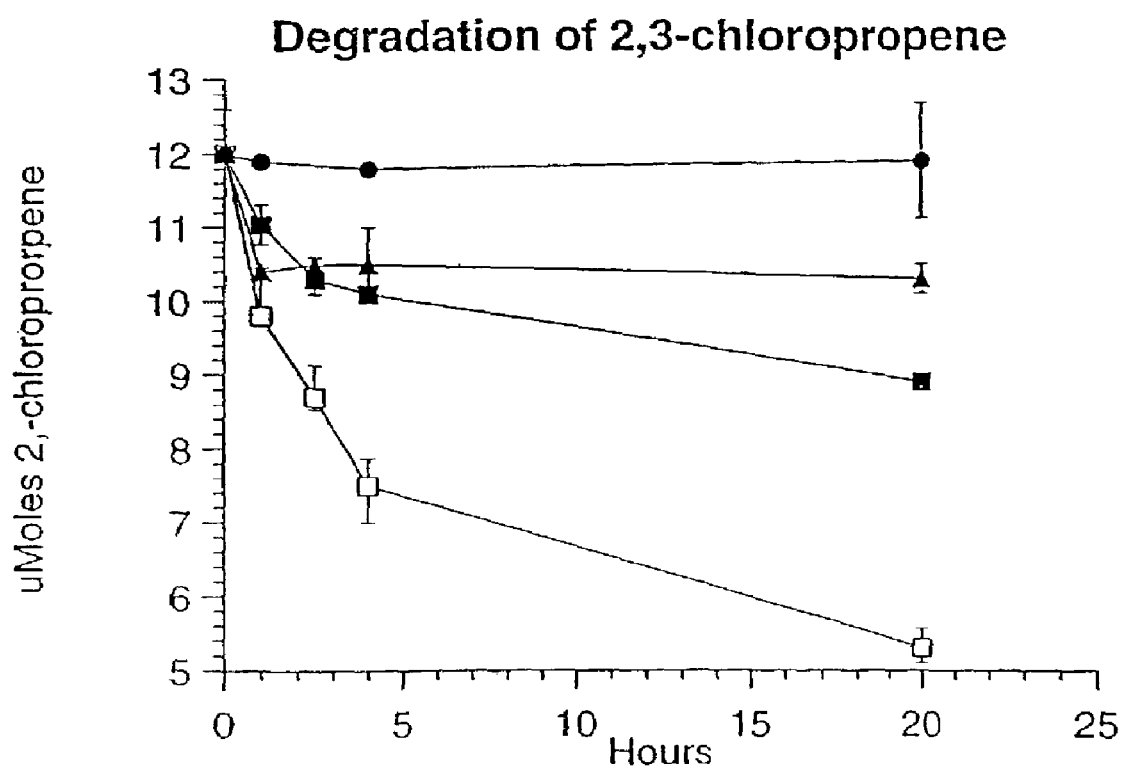

The stoichiometry of epoxide formation was evaluated by incubating toluene induced G4 with 4.4 μmoles of 1,3-butadiene and monitoring both butadiene and BME concentrations. Initially, there was a nearly stoichiometric conversion of butadiene to BME (>95%), followed by a decrease in BME concentration after the parental compound was degraded (FIG. 8). In contrast, when G4 was incubated with 2.2 μmoles of 2-butene, only 43% of the 2-butene degraded could be detected as the epoxide product. Efforts to detect 2-butene-1-ol in the liquid media were not successful.

Figure 7:
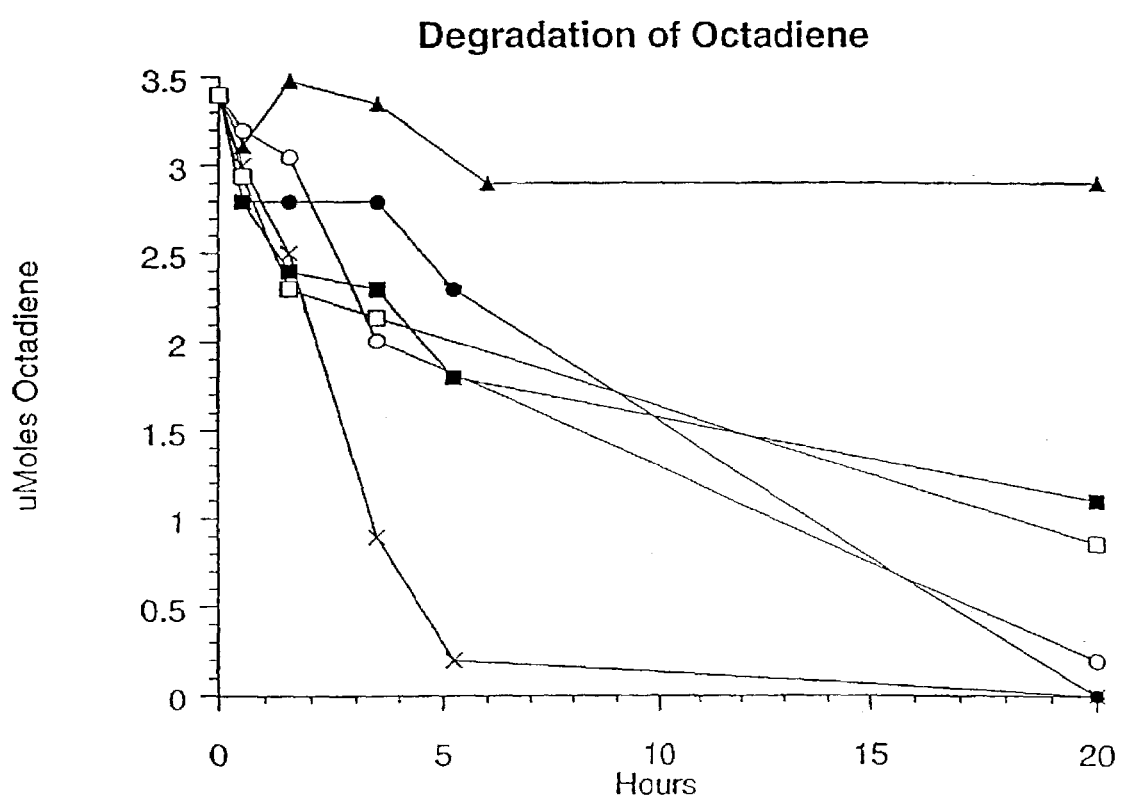

To determine if the disappearance of the epoxides was caused by chemical or enzymatic hydrolysis, BME was incubated with toluene-induced, or uninduced, cultures of strain G4. Induced cells incubated with pure BME degraded 8 μmoles of the substrate in the first hour, whereas uninduced cells of G4 oxidized less than 1 μmole in the same time period. When induced cells that were incubated in the presence of both toluene and BME, or butadiene and BME, they degraded 0.5 and 0.7 μmoles of BME in approximately 5 hr. (FIG. 7). The oxidation of both toluene and butadiene was unaffected by the presence of BME, but butadiene oxidation was inhibited by toluene. Similar results were obtained with ENVBF1, where the uninduced cells degraded less than 1.3 μmoles of BME in 24 hours, whereas induced cells oxidized 13.4 μmoles (data not shown). These findings are similar to those of van Hycklama et al. 1996, which stated that the MMO hydroxylase functions as a catalyst for the formation of the epoxides of ethene and cis-DCE, as well as a catalyst for the hydrolysis of these epoxides.

Enantiomeric Ratios of Biologically Produced Epoxides

The epoxides formed from the oxidation of 1-butene, 1-pentene, and 1,3-butadiene were analyzed by chiral chromotography, and the results of these analyses are presented in Table 5. Commercially available BME was composed of 24% R-enantiomer and 76% (+/−2%) S-enantiomer. The enantiomeric ratios of epoxides produced by the toluene oxygenases differed between the toluene oxidizing strains and substrate tested. All of the strains tested had high levels of enantio-selectivity during oxidation of 1-butene, with a tendency to produce the S-enantiomer. Strain KR1 (T4MO) produced only the S-enantiomer of butene epoxide, whereas another T4MO-producing strain, ENVPC5, produced 89% S-enantiomer and 11% R-enantiomer. The T3MO-producing strain PKO1 and the T2MO-producing strain G4 had a selectivity similar to ENVPC5.

The formation of enantiomerically pure BME from 1,3-butadiene was even more variable than the butene epoxide, but it also had a tendency toward the production of the S-enantiomer. The greatest selectivity occurred with strain G4 (T2MO) (91.9% S) and the least selectivity occurred with strain ENVPC5 (T4MO) (67.3% S).

The oxidation of 1-pentene showed the greatest variability in selectivity, but in each case, a greater percentage of the epoxide formed was of the R-enantiomer. The product distribution ranged from 100% formation of the R-enantiomer by strain G4, to a low of 54.2% R-enantiomer by strain KR1. Overall, the T2MO of G4 had the greatest specificity of the enzymes tested; exhibiting the greatest specificity of the tested strains when oxidizing butadiene and pentene, and second greatest specificity when oxidizing butene.

Example 2

Enantio-Selectivity of the Epoxidation Reactions

Because of the growing interest in enantio-pure feed stocks for both industrial and pharmaceutical chemical synthesis, we examined the enantio-selectivity of the epoxidation reactions catalyzed by the various toluene monooxygenases with 1-butene, 1,3-butadiene, and 1-pentene as the substrates. We found that when paired with the proper substrate, the toluene monooxygenases catalyze epoxidation reactions with a high degree of enantio-selectivity (Table 3). For example, when the T4MO of KR1 oxidized 1-butene, only one isomer could be detected, as was the case with G4 and 1-pentene. Of the 15 alkene/oxygenase pairs tested, 6 yielded epoxide products with >90% enantiomeric purity. Such highly selective oxidations may make this class of enzyme useful for industrial synthesis of optically active epoxides.

In this study we examined variants of TMO that oxidize the aromatic ring of toluene at all three possible positions, with three representatives, KR1, ENVPC5, and ENVBF1, of the T4MO variety. (Note: In a previous report (McClay et al., *Appl. Environ. Microbiol.*, 62:2716–2722 (1996)) we suggested that the toluene monooxygenase of ENVBF1 was a T2MO based on oxygen consumption studies following growth on toluene. We have since discovered that the cloned ENVBF1 toluene oxygenase genes produce p-cresol during oxidation of toluene.) The rate of alkene oxidation and the enantio-selectivity of the epoxides formed by these three toluene-4-monooxygenases varied widely. This suggests that there is no correlation between the regio-selectivity of toluene oxidation, and the enantio-selectivity of alkene oxidation catalyzed by a given enzyme. An analysis of the amino acid sequences and structures of the active site regions of the respective hydroxylases may provide a better understanding of the exhibited regio- and enantiomeric selectivity of the enzymes.

Example 3

Site-Specific Mutagenesis of Toluene Monooxygenase to Produce a Different Population of Enantio-Specific Epoxides Chemicals The chemicals 1-butene (99%), 1,3-butadiene 99%, 1-pentene (99%), toluene (98%), trichloroethylene (99%), 1,1,1-trichloroethane (98%), chloroform (98%), pyridine (99.9%), pentane (99%), styrene (98%), 3-chlorostyrene (98%), 4-chlorostyrene (99%) and IPTG (isopropyl-β-D-thiogalacto-pyranoside (99%) were obtained from Aldrich Chemicals (Milwaukee, Wis.). Methane and ethane were obtained from Air Gas Mid-Atlantic Inc. (Baltimore, Md.).

Growth and Preparation of Cells

The *Escherichia coli* strains DH10B and BL21(DE3) were maintained on LB agar and broth. When strain DH10B was used as the host for expression of cloned T4MO genes in degradation assays, the cultures were grown in LB broth supplemented with the appropriate antibiotic to maintain the degradative plasmid being studied. The cultures were harvested by centrifugation and resuspended in fresh LB broth to an optical density at 550 nm ($OD_{550}$) of 4, and IPTG was added to the cultures to a final concentration of 0.5 mM. Flasks containing the resuspended cultures were placed on a rotary shaker at 150 r.p.m., and incubated at 37° C. for 30–40 minutes to allow for full-expression of T4MO prior to beginning the degradation assays. The strain BL21 (DE3) was prepared in a similar fashion, except LB was substituted with basal salts medium (BSM) supplemented with 0.3% glycerol and 0.3% glutamate as a carbon source.

Site Directed Mutagenesis of T4MO

Cloning of the tmoA-F gene cluster from *P. mendocina* KR1 to create plasmid pRS184f has been described elsewhere (Pikus et al., *Biochemistry*, 36:9283–9289 (1997)). Table 4 presents PCR primers used in the site-directed mutagenesis protocols discussed in the present application. The PCR primers described in Table 4 were used to create the desired mutations in cloned T4MO genes of strain KR1. The mutations were created by using a two step PCR process. The polymerase chain reactions were performed using the VENT® DNA polymerase from New England Biolabs Inc. (Beverly, Mass.), and the reaction conditions recommended by the manufacturer. The cycling conditions were as follows: 30 seconds at 94° C., 30 seconds at 50° C., and 30–45 seconds at 72° C., for 37 cycles. In the first step, two primary polymerase chain reactions were performed. One of the PCR reactions amplified the upstream region of T4MO DNA encoding the hydroxylase by using the forward primer TMOU1 and a reverse primer that incorporated the desired mutation. The second reaction amplified the downstream portion of the hydroxylase DNA by using a forward primer that was the reverse anti-parallel homologue of the mutagenic primer used in the other reaction, and the downstream primer ENVP3. The mutagenic primers were designed so the creation of the desired mutation would result in the formation or deletion of a restriction enzyme recognition site overlapping the mutagenized codon. This was done to allow simple and rapid identification of clones with the desired mutation via restriction fragment analysis. The products of the primary PCR reactions were separated by gel electrophoresis and purified using a GFX PCR DNA and Gel Band Purification Kit (Pharmacia, Piscataway, N.J.), and then ligated and used as the templates in a second PCR with primers TMOU1 and ENVP3. The product of the second PCR was purified as before, digested with Eco RI and Bgl II, and ligated to similarly digested pRS184f. The ligation mixture was then used to transform DH10B. The transformation mixture was plated on LB agar supplemented with ampicillin. The plasmid DNA from individual colonies was isolated and analyzed by digestion with the appropriate restriction endonucleases to verify the presence of the desired mutations.

The DNA of two of the mutant isoforms, F176A and F196G, was sequenced to verify the creation of the desired mutations because the primers that created these mutations did not encode for the modification of the restriction pattern of the resulting clones. Another mutation, I224V/A, was generated with a degenerate primer that created either a valine or an alanine codon at position 224. It has not been determined which residue is present in this clone.

TABLE 4

PCR Primers

| Mutagenic Primers[a] | | Affected Restriction Site |
|---|---|---|
| I100C | 5'-tac ggc gcc tgc gca gtt | Fsp I |
| I100K | 5'-tac ggc gcg gcg gca gtt ggt-3' | Bss HII |
| V102T | 5'-gcc atc gca acc ggt gaa-3' | Age I |
| G103L | 5'-atc gca gtt ctc gag tat gca-3' | Xho I |
| A107S | 5'-gaa tat gct agc gta acc ggt-3' | Nhe I |
| Q141C | 5'-tgc gcc atg gcc agt tat gcc tgt ttt tc-3' | Pvu II deleted |
| Q141V | 5'-tgc gcc atg gcc agt tag tgc tgt ttt tc-3' | Pvu II deleted |
| F176A | 5'-gca ttt cgc tga tga cat cat tac c-3' | |
| F176L | 5'-aag cat ttc atc gat gac-3' | Cla I |

TABLE 4-continued

PCR Primers

| | | Affected Restriction Site |
|---|---|---|
| L192M | 5'-gtt gcg atc atg atg acg ttt tca-3' | Bsp HI |
| F194P | 5'-gtt gac gcc atc att cg-3' | |
| F196G | cgt ttt cag gcg aaa ccg-3' | |
| F196L | 5'-acg ttt tca ctc gaa acc-3' | Bst BI deleted |
| T201A | 5'-tca ttc gaa acc ggc ttc gcc aac atg cag-3' | |
| T201F | 5'-tca ttc gaa acc ggc ttc gcc aac atg-3' | |
| F205I | 5'-tca ttc gaa acc ggc ttc acc aac atg cag att ctt-3' | |
| N222Q | acg ttt gct cag ctg atc tcc-3' | Blp I |
| N222S | 5'-acg ttt gct agc ctg atc tcc-3' | Nhe I |
| I224V/A | 5'-tgc atg tcg cga ctc atc ggt ttg aat gct gga grc cag gtt-3' | Nru I |
| I224F | 5'-tgc atg tcg cga ctc atc ggt ttg aat gct gga gaa cag gtt-3' | Nru I |
| I227T | 5'-ctg atc tcc agt act caa acc gat-3' | Sca I |
| Q238I | 5'-cat gca caa att ggc gcc ccc gca-3' | Kas I |
| Non-Mutagenic Primers | | |
| Tmou 1 | 5'-cgg aat tct tta aac ccc aca ggc acg g-3' | Eco RI |
| P3 | 5'-atg ttg cac acg cag ggc aag gtt-3' | |
| 3Ncof | 5'-aac cgc cat ggc cag ctg-3' | Nco I |
| 3Bglr | 5'-gcc cag atc tat caa ggt gcg-3' | Bgl II |
| Sfir | 5'-aag gcc tga tcg gcc aa-3' | |
| Sfif | 5'-tgg gcc gcc cgg gcc aca-3' | |
| CYS1f | 5'-cgc aga att cgc cgg tca tta tct-3' | Eco RI |
| CYS2r | 5'-tgc tgg tcg ata tcc att gat gg-3' | Eco RV |

Restriction sites that were created or eliminated are underlined.
<sup>a</sup>Only the forward primers used for a site directed mutagenesis are shown because the reverse primers are antiparallel homologous to the forward primer.
<sup>b</sup>r = either t or c Screening for Indigo Formation Many oxygenases, including T4MO, catalyze the oxidation of the heterocyclic ring of indole (O'Connor et al., *Appl. Environ. Microbiol.*, 63:4287–4291 (1997); Eaton et al., *J. Bacteriol.*, 177:6983–6988 (year?); Enseley et al., *Science*, 222:167–169 (1983)), forming indoxyl. In the presence of oxygen, two indoxyl molecules condense, forming the dye indigo (Murdock et al., *Bio/technology*, 11:381–386 (1993)). The formation of indigo serves as the basis of a simple and sensitive screening assay to identify clones expressing active T4MO. *E. coli* converts excess tryptophan in LB media to indole, providing a substrate for cloned T4MO and the formation of indigo By comparing the rate and intensity of pigment accumulation in the wild type and mutant T4MO isoforms, the level of T4MO activity of the mutants can be estimated.

Substrate Degradation Assays

The substrate ranges of the T4MO mutants were determined by dispensing 5-ml aliquots of the cultures prepared as described above, in duplicate or triplicate, to 25-ml serum vials that were sealed with Teflon™ faced septa. The substrates (20% in dimethyl formamide or as pure gas) were injected through the septa with a gas tight syringe. The amount of substrate added to the vials was as follows: methane, 2 µMoles; ethane, 2 µMoles; pentane, 5 µMoles; pyridine 4.5 µMoles; styrene, 2 µMoles; 3-chlorostyrene, 2 µMoles; 4-chlorostyrene, 2 µMoles; 1,1,1-TCA, 50 nMoles; TCE, 200 nMoles; CF, 200–400 nMoles; toluene, 9–18 µMoles; 1-butene, 2.2 µMoles; 1,3-butadiene, 2.2 µMoles, and 1-pentene, 9 µMoles. The vials were incubated at 37° C. on a rotary shaker at 100 rpm. Following incubation, a 10–25 µl portion of the headspace gas was withdrawn through the septa and injected onto a Varian 3400 gas chromatograph (GC) (Walnut Creek, Calif.) equipped with a 30 m Vocol column (Supelco Inc. Bellefonte, Pa.) that was maintained at 160° C. The substrates were quantified with a flame ionization detector, except for TCA, TCE, and CF, which were measured with an electron capture detector.

Because site directed mutagenesis could affect the amount or activity of T4MO present in the host cells, we attempted to correlate the amount of TCE, CF or butadiene transformed by the mutants to the amount of toluene degraded by the same cells. This was accomplished by incubating subsamples of each T4MO mutant culture, with toluene and each of the target substrates. We used this data to relate the amount of TCE, CF, or butadiene transformed to the amount of toluene degraded by the same strain.

Determining the Enantiomeric Ratios the Monoepoxides

To determine the ratio of (R) and (S) epoxide isomers formed from the oxidation of the alkenes, samples were analyzed on a Varian 3400 GC equipped with flame ionization detector and a chiral column (RT-BDEXSE; Restek, Bellefonte, Pa.), that was maintained isocratically at 50° C. To insure that there was sufficient epoxide present for chiral analysis, alkene degradation was monitored by standard GC analysis. When approximately 90% of the added substrate had been degraded, a portion of the headspace gas was used for chiral analysis.

The examples which follow demonstrate alteration in catalytic activity by site directed modification of active site amino acids.

The results of these studies are presented in Table 5.

Example 4

Site-Directed Mutagenesis of Ile$^{100}$ (I100)

Crystallographic studies of MMO led to the hypothesis that homologue of the T4MO residue I100 (L110 in MMO) functions as part of a "gate" that controls the access of reactants and products to and from the catalytic center on the MMO hydroxylase (Rosenzweig, et al., *Proteins*, 29:141–152 (1997)). When the catalytic center is in the oxidized form the "gate" is closed, whereas it is open when the diiron center is reduced. This action may control the timing of the reactants entering the active site to prevent the larger organic substrates from binding in the active site before diatomic oxygen is bound and activated. Premature entry of organic substrates could interfere with the activation of $O_2$, thereby inhibiting catalysis. Alternately, I100 could function as a clamp, holding the substrate in close proximity to the diiron center, ensuring proper orientation of the intended substrate.

We made two mutations at this site; I100R and I100C. In the I100R mutation, the R chain of the substituting amino acid is approximately 76% longer than the native isoleucine, and it terminates with a charged residue rather than a hydrophobic one. This substitution completely inactivated the enzyme. Conversely, the R side chain of the mutant I100C is 28% smaller, and more polar, than the wild type isoleucine. This isoform efficiently converted indole to indigo, as indicated by the rapid production of an intense blue color on LB media, but it decreased activity towards toluene, TCE, and butadiene (Table 5). The TCE ratio (nM TCE degraded/µM toluene degraded) increased to 335% that of the wild type, while butadiene ratio (µM butadiene/µM toluene degraded) remained the same. Furthermore, when the I100C mutant oxidized butadiene, the ratio of (R) and (S) enantiomers of butadiene monoepoxide (BME) produced was nearly the exact opposite of the ratio of the wild type (Table 5). The BME produced by the wild type enzyme was 33% R form and 67% (+/−1%) S form, whereas the BME produced by the I100C mutant was 60% R form and 40% (+/−5%) S form.

These results support the gating hypothesis proposed by Rosenzwieg et al (*Proteins*, 29:141–152 (1997)). By making the side chain of this residue longer and charged, oxygenase activity was abolished, possibly because the side chain was too large to allow entrance of reactants regardless of the position of the gate. When the side chain was decreased in size (i.e, I100C), the enzyme remained active, but the level of activity of the isoform towards the substrates tested was decreased relative to the wild-type enzyme. With the smaller residue in this position, more small organic molecules might enter the active site prematurely and block activation of $O_2$. Alternately, the smaller, polar residue may not be able to hold and/or orient the small, primarily hydrophobic substrates in the active site. The smaller residue had a lesser effect on the oxidation of a larger substrate, indigo.

The alterations in the TCE ratio and the product distribution that results from the oxidation of butadiene suggest that the I100 residue participates in maintaining the proper orientation of substrates within the active site, in addition to possibly serving as a gating component. The ratio of TCE degraded to toluene degraded was greatly reduced, but the ratio of butadiene oxidized to toluene degraded was not reduced, possibly because of the larger size of butadiene relative to TCE. The orientation of the butadiene in the active site must have been altered in the mutant, however, as indicated by the alteration in the enantiomeric selectivity. It appears that butadiene can be positioned in the active site in an orientation that allows oxidation of one of the double bonds, whereas TCE is not held in the proper orientation in the I100C isoform.

Example 5

Site-Directed Mutagenesis of $Gly^{103}$ (G103)

Amino acid alignments comparing MMO and two AMO sequences revealed that, as the size of the residue in the position homologous to G103 of T4MO increases (glycine, alanine, valine), so does the enantio-selectivity of propene oxidation (Zhou et al., *FEBS Letters*, 430:181–185 (1998)). T4MO and MMO have the smallest possible amino acid in this position (glycine), whereas T2MO has a larger residue (leucine) (FIG. 1). The results also showed that T2MO oxidized butadiene with greater enantio-selectivity than T4MO, lending support to the hypothesis that this residue has an effect on the enantio-selective oxidation of alkenes. To test whether increasing the size of the residue effects enantiometric selectivity, the glycine at position 103 of T4MO was replaced with a leucine. The enantio-selectivity of butadiene oxidation with the G103L isoform was 134% of the wild type (Table 5). The BME produced by the wild type enzyme was 67% S enantiomer, and the BME produced by the G103L isoform was 90% (+/−3%) S enantiomer. This was similar to the enantiomeric specificity of the T2MO of *Burkholderia cepacia* G4 which produced 91.9% (+/−1.4) of the S enantiomer. These results appear to confirm that the amino acid residue corresponding to G103 of T4MO participates in enantio-selective oxidations of alkenes.

The G103 residue also appeared to be involved in substrate specificity. Although the G103L isoform produced large amounts of indigo, as indicated by the formation of dark blue colonies on LB, it did not oxidize TCE (Table 5). It did, however, oxidize butadiene much better than the wild type isoform, as indicated by a butadiene ratio 375% greater than the wild type enzyme (Table 5). These changes in activity may be related to a change in the size or shape of the enzyme active site that prevents efficient docking or orientation of TCE relative to the diiron center, while improving the orientation of butadiene.

*E. coli* containing plasmid pRS184f (G103L) (ATCC PTA-107) was deposited with the ATCC on May 21, 1999. This plasmid encodes the G103L isoform described above.

Example 6

Site-Directed Mutagenesis of $Ala^{107}$ (A107)

The alanine residue at position 107 in the T4MO hydroxylase is conserved in all of the monooxygenases we studied (FIG. 1), suggesting that it confers some evolutionary advantage in these diiron monooxygenases. We replaced the hydrophobic alanine with the longer and more polar serine residue, and the BME produced from the resulting A107S isoform was 84% S enantiomer. This represented a 125% greater selectivity than the wild type isoform (Table 5). Similarly, the selectivity of pentene oxidation was increased to 137% of the wild type (Table 5). The A107S mutation, like the mutant G103L, caused a large increase in the observed butadiene ratio (220% increase) (Table 5). In contrast to the G103L mutation, however, the A107S mutation increased the TCE ratio by 16.

The results of our experiments, particularly the change in product distribution, suggest that the conserved alanine at positions corresponding to 107 in T4MO is somehow involved in positioning substrates in the active sites. Unlike G103L, the mutation A107S changed two physical parameters, length and polarity, so it is unclear which property is responsible for the observed change in enantio-selectivity and substrate specificity. Furthermore, it is not clear why related enzymes that oxidize such a diverse range of substrates, from methane to xylene and indole, would retain alanine at this position if it were not somehow advantageous.

*E. coli* containing plasmid pRS184f (A107S) (ATCC PTA-106) was deposited with the ATCC on May 21, 1999. This plasmid encodes the A107S isoform described above.

Example 7

Site-Directed Mutagenesis of $Gln^{141}$ (Q141)

The residue in MMO homologous to Q141 in T4MO is a cysteine which is believed to be important in the process of methane oxidation (Zhou et al., *FEBS Letters*, 430:181–185 (1998)). The hydrogen of the cysteine sulfhydril group may be removed at some step in the catalytic cycle, leaving a cysteine radical that facilitates the hydroxylation of methane (Feig et al., *Chem. Rev.*, 94:759–805 (1994)). With the exception of T2MO, the aromatic oxygenases have a glutamine at this position, while T2MO and the alkene monooxygenases have acidic residues. It has been proposed that the absence of a cysteine at this position accounts for inability of the aromatic and alkene monooxygenases to oxidize unsaturated hydrocarbon methane (Zhou et al., *FEBS Letters*, 430:181–185 (1998)), in spite of the fact that T4MO is known to oxidize CF, 1,2-DCA, and the unsaturated methyl groups of toluene and xylene (Pikus et al., *Biochemistry*, 36:9283–9289 (1997); McClay et al., *Appl. Environ. Microbiol.*, 62:2716–2722 (1996)). To mimic the hydroxylase of MMO, we created the mutations Q141C and Q141V. Neither of these mutations allowed T4MO to oxidize methane, but the Q141C mutation did affect the oxidation of a number of aromatic compounds (Pikus et al., Biochemistry, 36:9283–9289 (1997)). In this study we found that the Q141C mutation increased the TCE ratio by 40%, and the butadiene ratio by 70% (Table 5). The change in the enantio-selectivity of butadiene oxidation was negligible, falling with in the range of analytical error. The mutation Q141V had a negligible impact on the TCE ratio, but it increased the butadiene ratio 3.4-fold (Table 5). It also led to a decreased specificity in butadiene oxidation with only 56% of the resulting BME of the S enantiomer (Table 5).

Both the Q141C and Q141V mutations decreased the size and dipole moment of the R chain, relative to the wild type. The result of both mutations was an overall relaxed specificity observed in the hydroxylase. Because charged, polar, and hydrophobic residues are tolerated in this position of T4MO, the functional group of this residue may not perform a function required for substrate oxidation in T4MO, though it may act differently in MMO.

Example 8

Site Directed Mutagenesis of Phe$^{176}$ (F176)

Another residue whose position suggested a gating function was F176 (F188 in MMO) (Rosenzweig et al., Proteins, 29:141–152 (1997)). We made two substitutions at this position to probe the significance of this residue. The mutant F176A catalyzed the very slow formation of indigo, but was inactive towards all other substrates tested (Table 5). The F176I mutant was much more active than F176A, but it accumulated low levels of indigo relative to mutant I100C. The TCE and butadiene ratios of F176I were 439% and 151% greater than the ratios of the wild type isoforms, respectively, primarily due to a decreased toluene oxidation activity. The enantio-selectivity of the enzyme was slightly decreased (7%) relative to the wild-type isoform.

The results of these experiments do not clearly demonstrate a role for F176, but they do suggest that it is an important residue in the active site complex. Making the residue smaller either abolished activity completely, or it resulted in a great decrease in toluene oxidizing activity. Toluene is presumably the natural substrate for T4MO, and toluene oxidation is very regio-specific, with the primary reaction product being para-cresol (Pikus et al., Biochemistry, 36:9283–9289 (1997)). Even slight changes in the active site spatial conformation could alter docking of the substrate, thereby either inhibiting oxidation, or resulting in a change in the regio-specificity of oxidation. The same alterations might have less impact during oxidation of alternative substrates like TCE and butadiene that might naturally be less stringently bound in the active site.

Example 9

Site-Directed Mutagenesis of Phe$^{196}$ (F196)

In T4MO the residue F196 is located adjacent to Q197. In MMO the amino acid analogous to Q 197 participates in the binding of the iron atoms that make up the catalytic center of the enzyme. In the related diiron enzymes in plants, fatty acid desaturase and fatty acid hydroxylase, the difference in the catalytic activity of the two enzymes is dictated by the active site geometry (Broun et al., Science, 282:1315–1317 (1998)). Subtle differences impacting the coordination of the diiron center, or the distance-maintained between the substrate and the catalytic center are believed to dictate whether these enzymes function as desaturases or hydroxylases. Because of its proximity to the diiron center, altering F196 could lead to changes in catalytic activity (Zhou et al., Appl. Environ. Microbiol., 65:1589–1595 (1999)). We generated two mutations at site F196; F196G and F196L. The F196G mutant produced very low levels of indigo (detectable only after 7 days of incubation), and it was inactive on all other substrates tested. The F196L mutant, however, retained a significant level of activity. Although similar to the F176I isoform, it had a reduced capacity for indigo formation; forming pinkish/purple colonies instead of the dark purple colonies of the wild type. The TCE ratio of F196L was 1.5 fold greater than the wild type enzyme due, but the butadiene ratio was 60% less than the wild type isoform (Table 5). The enantio-selectivity of butadiene oxidation-decreased by 4% (Table 5).

The F196L mutation did have a measurable effect on CF oxidation. In initial assays with F196L and the wild type T4MO clones, cells were grown and incubated with CF in LB broth. Both the wild type enzyme and the F196L mutant degraded toluene immediately, but CF degradation did not occur until after a lag period of approximately 40 minutes, and it proceeded at a greater rate than achieved with the wild-type isoform. When the amount of CF degraded by the wild type isoform was compared to the amount of toluene degraded by the same strain, there was a linear correlation (FIG. 2). CF degradation, however was completely inhibited during the initial period of the incubation, but it was linear after the lag period (FIG. 2).

The inhibition of CF degradation seen with the F196L isoform when assayed in LB media is similar to the apparent competitive inhibition of CF degradation observed when strain KR1 was incubated with both TCE and CF (McClay et al., Appl. Environ. Microbiol., 62:2716–2722 (1996)). Furthermore, in LB broth cultures, indigo does not appear to form in the presence of toluene, but it did form in cultures with chloroform, suggesting that indole interferes with CF degradation, but not toluene oxidation.

When we performed the same assays in minimal media to prevent the formation of indole from LB, the F196L isoform degraded CF much more rapidly than the wild type isoform. The F196L isoform oxidizing 15.9 μMoles toluene and 348 nMoles CF compared to the 15.1 μMoles toluene and 201 nMoles CF degraded by the wild type isoform.

Example 10

Site-Directed Mutagenesis of Thr$^{201}$ (T201)

Like residue A107, all of the diiron oxygenases considered in this study have a threonine at the position analogous to the T201 of T4MO (FIG. 1). It has been proposed that this threonine is required for the active scission of the O=O bond (Feig et al., supra). To explore this hypothesis we replaced T201 with a series of amino acids, including serine (T201S). The substitution of threonine with a serine decreases the bulk of the R chain, leaving room for greater mobility of the substrates in the active site, but retaining the hydroxyl group thought to be involved in $O_2$ activation. The TCE and butadiene ratios obtained from this isoform were the same as those obtained with the wild type isoform (Table 5). However, the enantio-selectivity of butadiene oxidation was shifted, favoring the production of the (R)-enantiomer by a 58 to 42 ratio (Table 5). These ratios were similar to the ratio seen with the mutant I100C, and nearly the opposite of the wild type ratio. Pentene epoxidation was similarly effected. Whereas the wild type isoform had a pentene epoxide entiomeric ratio of 54% (R) 46% (S), the T201S had an enantiomeric ratio of 40% (R), 60% (S) (Table 5). These results suggest that the T201 residue of T4MO is involved in positioning alkenes in the active site.

Example 11

Site-Directed Mutagenesis of Other Amino Acids in the Putative Active Site of T4MO We mutated 4 other amino acid residues that were predicted from our model derived from the MMO crystal structure to be in the active site of T4MO, but for which no particular function has been proposed by others. The mutation L192M substituted a larger amino acid for the native residue, and led to a 6% increase in the selectivity of butadiene oxidation (Table 5) and 2.7 fold increase in the TCE ratio (Table 5). The butadiene ratio for this mutant was not determined. Like the mutations F176A and F196G discussed above, mutations to two active site residues, I224V/A and I227T, decreased the activity of the oxygenase. All four of these mutants produced low levels of indigo, but generally lacked the ability to oxidize any of the other substrates tested (Table 5). One exception was the I227T isoform, which retained a low level of TCE oxidation activity (Table 5). Since this mutant failed to oxidize toluene, the TCE ratio of this mutant was infinitely large.

Example 12

Site-Directed Mutagenesis of Amino Acid Residues Outside of the Active Site of T4MO We also mutated two residues that were not located within the putative active site of T4MO. Because of the positioning of the residue V102, it probably does not come into direct contact with T4MO substrates. However it is located between two potentially important residues (I100 and G103) discussed above. We replaced the native valine with the more polar residue threonine to determine if small perturbations in this region of the alpha-helix would be communicated to the active site. The isoform, V102T, remained highly active on all substrates (Table 5), and had a small increase (5%) in the enantio-selectivity of butadiene oxidation (Table 5). Also, the TCE ratio of the V102T isoform was 70% of wild type, and the butadiene ratio was 38% of the wild type isoform (Table 5). The residues homologous to N222 in T4MO are serines or threonines in the oxygenases examined here (FIG. 1), with the exception of the AMO of PY2 which also has an asparagine. We created the mutations N222S and N222Q to determine if this residue performs an important function. The mutant N222S has a TCE ratio of 10.3 and a butadiene ratio of 0.059 (Table 5), both decreased relative to the wild type, but the mutation did not alter enantio-selectivity of butadiene oxidation (Table 5). The mutant N222Q, incorporates an R chain that has the same functional group as the wild type asparagine, but is longer by one carbon, and is inactive. Since the chemical properties of the mutated R-chains that result in an inactive isoform are the similar to those of the native residue, whereas the active mutant isoform has a different functional group, it appears that size of the amino acid at this position effects catalytic activity. Perhaps the increase in the bulk of the R chain of N222Q causes a distortion in the a-helical bundles, while the decreased size of the R chain of the mutant N222S residue allows a more normal conformation, thereby preserving activity.

Example 13

Preparation of Recombinant Bacteria Containing Toluene Monooxygenases

This example is illustrative of a procedure for preparing a recombinant microorganism that can oxidize alkenes to form epoxides.

In particular, this example presents a procedure used to introduce the toluene monooxygenase genes from *P. mendocina* KR1 into *E. coli*.

This same procedure may be used to prepare other recombinant microorganisms containing the toluene monooxygenase genes or similar genes which encode a non-haem diiron monooxygenase capable of oxidizing an alkene to an epoxide.

Unless otherwise noted, all molecular biological manipulations were performed by methods known to those skilled in the art, essentially as described by Sambrook, et al. (*Molecular Cloning, A Laboratory Manual*, 2nd Edition, Cold Spring Harbor Laboratory Press, 1989.) The DNA sequences of tmo A-E and tmo F from *P. mendocina* KR1 have been reported previously. (Yen, K.-M., et al., 1991. *J. Bacteriol.* 173:5315–5327; Yen, K. M. and M. R. Karl. 1992. *J. Bacteriol.* 174:7253–7261.) Total genomic DNA of *P. mendocina* KR1 was isolated using the method of Wilson (Wilson, K. 1993. p. 2.4.1–2.4.5. in F. M. Ausubel, et al., (eds.), *Current Protocols in Molecular Biology*. Current Protocols, Brooklyn, N.Y.). The first five genes (tmo A-E) were amplified by using polymerase chain reaction (PCR) with primers TMOU 1 (5'-CGGAATTCTTTAAACCCCA-CAGGCACGG-3') and TCED 3 (5'-GCGAATTC-GATAATGGTTTGCACTGCCA-3') which incorporated EcoRI restriction sites on each end of the 3652 bp amplified fragment.

PCR was performed using a GeneAmp kit (Perkin Elmer, Foster City, Calif.) and reaction conditions recommended by the manufacturer. Cycling conditions were: 1 min at 94° C., 30 sec at 50° C., and 3 min at 71° C., for 25 cycles. Amplified DNA was digested with EcoRI (New England Biolabs, Beverly, Mass.), and ligated to similarly digested pUC18Not. The ligation mixture was used to transform *E. coli* JM109. Clones were selected by plating the cells onto LB agar-supplemented with ampicillin (100 µg/ml), and then replica plating onto LB plates that contained 100 µg/ml indole, and 20 µg/ml isopropyl-β-D-thiogalactopyranoside (IPTG). A single colony that formed a blue color from the conversion of indole to indigo, indicating monooxygenase activity, and contained the 3652 bp insert of tmo A-E, as determined by restriction analysis, was selected for further use and designated pRS184. (Ensley, B. D. et al., 1983. *Science* 222:167–169; Yen, K. -M. et al., 1991. 173:5315–5327.)

To add the sixth gene encoding TMO F to the tmoA-E cluster, total chromosomal DNA of *P. mendocina* KR1 was digested with EcoRV and XmaI and separated on an agarose gel. Fragments ranging from 2 to 3 kb were excised from the gel, purified using the Qiaex system (Qiagen, Chatsworth, Calif.), ligated to similarly digested pRS184, and used to transform *E. coli* DH5a. Positive clones were selected for their ability to convert indole to indigo, as previously described. Restriction analysis of positive clones confirmed that they contained the 4727 bp tmoA-F insert. The plasmid construct was designated pRS184f (Pikus et al., *Biochemistry*, 35:9106–9119 (1996)). The pRS184f construct was then digested with EcoRI and SmaI and the tmoA-F genes were ligated to similarly digested pVLT31 and used to transform *E. coli* DH5α, and *E. coli* DH10B. This plasmid was designated pRS202.

TABLE 5

Characterization of Mutant T4MO Isoforms.

| Mutation | Change in side chain size | Change dipole characteristic | μM Toluene degraded | nM TCE degraded | μM Butadiene degraded | % butadiene epoxide formed | | | Indigo formation |
|---|---|---|---|---|---|---|---|---|---|
| | | | | | | R | S | | |
| Wild type | NA | NA | 8.6 (0.03) | 134 (8.8) | 0.91 (0.19) | 33 | 67 (1) | N = 7ᶜ | ++ |
| I100K | increase | NP > charged | xx | xx | xx | xx | xx | | -- |
| I100C | decrease | NP > polar | 1.69 (0.4) | 88 (4.4) | 0.17 (0.05) | 60 | 40 (5) | N = 4 | ++ |
| V102T | increase | NP > polar | 8.8 (0.11) | 92 (4.7) | 0.34 (0.08) | 28 | 72 (1) | N = 2 | ++ |
| G103L | increase | none | 3.2 (0.47) | 0.0 | 1.2 (0.04) | 10 | 90 (3) | N = 4 | ++ |
| A107S | increase | NP > polar | 7.7 (0.48) | 139 (3.5) | 1.9 (0.08) | 16 | 84 (2) | N = 6 | ++ |
| Q141V | decrease | charged > NP | 2.66 (0.59) | 46 (6.4) | 0.91 (0.12) | 44 | 56 (1.6) | N = 4 | ++ |
| Q141C | decrease | charged > polar | 7.03 (0.29) | 147 (0.83) | 1.2 (0.3) | 37 | 63 (5) | N = 4 | ++ |
| F176L | decrease | none | 2.2 (0.07) | 150 (2.9) | 0.35 (0.12) | 40 | 60 (1) | N = 5 | ++ |
| F176A | decrease | none | xx | xx | xx | xx | xx | | ++ |
| I180F | increase | none | nd | nd | nd | 42 | 58 (2) | N = 2 | ++ |
| I192M | increase | none | 4.7 (0.69) | 197 (1.2) | nd | 27 | 73 (4) | N = 2 | ++ |
| F194P | decrease | none | xx | xx | xx | xx | xx | | -- |
| F196L | decrease | none | 6.8 (0.09) | 157 (10) | 0.28 (0) | 37 | 63 (9) | N = 4 | ++ |
| F196G | decrease | none | xx | xx | xx | xx | xx | | +/- |
| T201S | decrease | none | 8.7 (0.21) | 138 (1.6) | 1.1 (0.04) | 58 | 42 (8) | N = 7 | ++ |
| T201A | decrease | polar > NP | nd | nd | nd | nd | nd | | ++ |
| T201F | increase | polar > NP | nd | nd | nd | nd | nd | | ++ |
| T201Q | increase | polar > charged | nd | nd | nd | nd | nd | | ++ |
| F205I | decrease | none | nd | nd | nd | 28 | 72 (3) | N = 2 | ++ |
| N222S | decrease | charged > polar | 9.1 (0.03) | 94 (3.3) | 0.54 (0.8) | 33 | 67 (0) | N = 2 | ++ |
| N222Q | increase | none | xx | xx | xx | xx | xx | | -- |
| I224V/A | decrease | none | xx | xx | xx | xx | xx | | +/- |
| I224F | increase | none | 9.08 (0.16) | 171 (12) | 0.87 (0.3) | 41 | 59 (3) | N = 2 | ++ |
| I227T | decrease | NP > polar | 0 | 17 (0) | 0 | xx | xx | | ++ |
| Q238I | decrease | charged > np | 8.1 (0.06) | 185 (2.4) | 0.91 (0.07) | 39 | 61 (2) | N = 2 | ++ |

We claim:

1. A method for preparing a single enantiomeric species of an epoxide comprising contacting an alkene with a native non-haem diiron-containing monooxygenase and recovering said epoxide produced.

2. The method of claim 1 wherein said monooxygenase is a toluene monooxygenase.

3. A method for preparing an epoxide comprising contacting an alkene with a mutated non-haem diiron-containing monooxygenase and recovering said epoxide produced.

4. The method of claim 3 wherein said monooxygenase is a toluene monooxygenase.

5. A method for preparing an epoxide comprising contacting an alkene with a non-haem diiron-containing monooxygenase mutated by the substitution of at least one amino acid residue.

6. The method of claim 5 wherein said monooxygenase is a toluene monooxygenase.

7. A process for producing a desired ratio of epoxide enantiomers comprising contacting an alkene with a mutated non-haem diiron monooxygenase.

8. A process for producing a desired ratio of epoxide enantiomers comprising contacting an alkene with a native non-haem diiron monooxygenase.

9. The process of claim 7, wherein said desired ratio is 0–100:100–0 of R:S enantiomers.

10. The process of claim 8, wherein said desired ratio is 0–100:100–0 of R:S enantiomers.

* * * * *